(12) United States Patent
Lipkin et al.

(10) Patent No.: US 7,635,720 B2
(45) Date of Patent: *Dec. 22, 2009

(54) PROSTAGLANDIN ANALOG COMPOSITIONS TO TREAT EPITHELIAL-RELATED CONDITIONS

(75) Inventors: Pamela Lipkin, New York, NY (US); Beverly Lubit, Kinnelon, NJ (US)

(73) Assignee: Meta Cosmetics, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/235,887

(22) Filed: Sep. 23, 2008

(65) Prior Publication Data

US 2009/0111889 A1 Apr. 30, 2009

Related U.S. Application Data

(60) Provisional application No. 60/984,198, filed on Oct. 31, 2007.

(51) Int. Cl.
*A61K 31/165* (2006.01)
(52) U.S. Cl. .................................................. 514/622
(58) Field of Classification Search ........................ None
See application file for complete search history.

(56) References Cited

U.S. PATENT DOCUMENTS

| | | | | |
|---|---|---|---|---|
| 3,987,087 | A | * 10/1976 | Bundy | .................. 554/216 |
| 4,352,760 | A | 10/1982 | Maxey | |
| 4,812,457 | A | * 3/1989 | Narumiya et al. | ........ 514/226.2 |
| 5,977,173 | A | 11/1999 | Wos | |
| 6,048,895 | A | 4/2000 | Wos | |
| 2002/0172693 | A1 | 11/2002 | DeLong | |

OTHER PUBLICATIONS

Hogan et al.; "Male Pattern Baldness"; 2000; Southern Medical Journal; 93(7): 657-662.*
Bergstrom et al.; The Prostaglandins: A Family of Biologically Active Lipids; 1968; Pharmocological Reviews; 20; 1-48.*
Cayman Chemical Company; "Product Information: (+)-Cloprostenol"; 2005; Catalog No. 16765; accessed online Jan. 23, 2008: http://www.caymanchem.com/pdfs/16765.pdf.*
Serrero, et al.; "Prostaglandin F2alpha Receptor(FP Receptor) Agonists Are Potent Adipose Differentiation Inhibitors for Primary Culture of Adipocyte Precursors in Defined Medium"; Biochem. Biophys. Res. Comm.; 1997; 233: 200-202.*
Hovgaard et al.; "Drug Delivery Studies in Caco-2 Monolayers, Synthesis, Hydrolysis, and Transport of O-Cyclopropane Carboxylic Acid Ester Prodrugs of Various Beta-Blocking Agents"; 1995; Pharmaceutical Research; 12(3): 387-392.*
Patani et al.; "Bioisosterism: A Rational Approach in Drug Design"; 1996; Chem. Rev.; 96: 3147-3176.*
Tosti et al.; "Hypertrichosis of the eyelashes caused by bimatoprost"; 2004; J. Am. Acad. Dermatol.; 51:S149-50.*
Mehta et al.; "Cutaneous latanoprost in the treatment of alopecia areata"; 2003; Eye; 17:444-446.*

* cited by examiner

*Primary Examiner*—Brandon J Fetterolf
*Assistant Examiner*—Timothy P Thomas
(74) *Attorney, Agent, or Firm*—Greenberg Traurig, LLP

(57) ABSTRACT

The present invention relates to the formulation and delivery of prostaglandin analogs to treat epithelial-related condition. In some embodiments, the compositions of the invention are used to stimulate hair growth. In some embodiments, the compositions of the invention are used to restore hair color to depigmented hair.

13 Claims, No Drawings

PROSTAGLANDIN ANALOG COMPOSITIONS TO TREAT EPITHELIAL-RELATED CONDITIONS

CROSS-REFERENCE TO RELATED APPLICATIONS

This application claims the benefit of U.S. Provisional Application No. 60/984,198, filed Oct. 31, 2007, the contents of which are incorporated by reference in their entirety.

FIELD OF THE INVENTION

The present invention relates to the formulation and delivery of prostaglandin analogs to treat epithelial-related conditions. In some embodiments, the compositions of the invention are used to stimulate hair growth. In some embodiments, the compositions of the invention are used to restore hair color to depigmented hair.

BACKGROUND OF THE INVENTION

Hair, a filamentous outgrowth of protein found only on mammals, is integral to our body image and can have a profound influence on our self-esteem and self-confidence. The hair of non-human mammal species is commonly referred to as fur. In some species, hair is absent at certain stages of life.

Hair grows from hair follicles deep in the dermis and projects from the epidermis of the skin. Human skin has two types of hair: vellus hair and terminal hair. Much of human hair is short, underpigmented vellus hair rather than terminal hair. The most noticeable part of human hair is the hair on the head, which can grow longer than on most mammals and is more dense than most hair found elsewhere on the body. The term "scalp" refers to the integument of the upper part of the head, usually including the associated subcutaneous structures. The scalp is the anatomical area bordered by the face anteriorly and the neck to the sides and posteriorly.

Vellus hair is short, fine, "peach fuzz" body hair. It is a very soft, generally pale, and short hair that grows in most places on the human body in both sexes. It is usually less than two cm long and the follicles are not connected to sebaceous glands. It is most easily observed in women and children, as they have less terminal hair to obscure it. It is also found in pre-adolescents and in male pattern baldness.

Terminal hair is developed hair, which is generally longer, coarser, thicker and darker than the shorter and finer vellus hair. Phases of growth in terminal hair are more apparent than in vellus hair; it generally has a longer anagen phase. It has associated sebaceous glands, whereas a vellus hair may not. Under certain conditions, such as puberty, some vellus hair may become androgenic hair. Under other conditions, such as male pattern baldness, it may revert to a vellus-like state.

Each hair comprises two structures: the follicle in the skin and the shaft we see. The follicle contains several layers. At the base of the follicle is a projection called a papilla, which contains capillaries, or tiny blood vessels, that feed the cells. The living part of the hair, the area surrounding the papilla called the bulb, is the only part fed by the capillaries. The cells in the bulb divide every 23 to 72 hours, faster than any other cells in the body. The follicle is surrounded by two sheaths—an inner and outer sheath. These sheaths protect and mold the growing hair shaft. The inner sheath follows the hair shaft and ends below the opening of a sebaceous (oil) gland, which produces sebum, a natural conditioner and sometimes an apocrine (scent) gland. The outer sheath continues all the way up to the gland. An erector pili muscle attaches below the gland to a fibrous layer around the outer sheath. When this muscle contracts, it causes the hair to stand up.

The primary component of the hair fiber is keratin. Keratins are proteins, long chains (polymers) of amino acids. The hair shaft contains three layers of keratin. The inner layer, which is called the medulla, may not be present. The next layer is the cortex, which makes up the majority of the hair shaft. The outer layer is the cuticle, which is formed by tightly packed scales in an overlapping structure similar to roof shingles. Most hair conditioning products attempt to affect the cuticle. Pigment cells are distributed throughout the cortex and medulla giving the hair its characteristic color.

The term "eyebrow" refers to an area of coarse skin hairs above the eye that follows the shape of the brow ridges. The main function of the eyebrow is to prevent moisture, mostly salty sweat and rain, from flowing into the eye, an organ critical to sight. The typical curved shape of the eyebrow (with a slant on the side) and the direction in which eyebrow hairs are pointed, make sure that moisture has a tendency to flow sideways around the eyes, along the side of the head and along the nose. Eyebrows also prevent debris such as dandruff and other small objects from falling into the eyes, as well as providing a more sensitive sense for detecting objects being near the eye, like small insects. Eyebrows also have an important facilitative function in communication, strengthening facial expressions such as surprise, confusion, or anger.

The terms "eyelash" and "lash" are used interchangeably to refer to one of the hairs that grow at the edge of the eyelid. Eyelashes protect the eye from debris and provide a warning that an object (such as an insect or dust mite) is near the eye (which then is closed reflexively).

The inside of the nose contains small hairs called cilia. These cilia and nasal mucus clean the air drawn into the nose of the microscopic particles we inhale, including dust, pollen, and pollutants, for ultimate passage to the lungs.

Hair Biology

There are three stages of hair growth: catagen, telogen, and anagen.

Anagen is the active growth phase of the hair during which the cells in the root of the hair are dividing rapidly. Anagen hairs are anchored deeply into the subcutaneous fat and cannot be pulled out easily. When a new hair is formed, it pushes the club hair up the follicle and eventually out. During this phase the hair grows about 1 cm every 28 days. Scalp hair stays in this active phase of growth for 2-6 years. Human subjects that have difficulty growing their hair beyond a certain length have a short active phase of growth. Human subjects that have very long hair have a long active phase of growth. The hair on the arms, legs, eyelashes, and eyebrows have a very short active growth phase of about 30-45 days, which is why they are so much shorter than scalp hair.

The anagen phase is followed by a catagen phase. The catagen phase is a transitional stage that lasts for about 2-3 weeks. About 3% of all hairs are in this phase at any time. During this time growth stops and the outer root sheath shrinks and attaches to the root of the hair. This is the formation of what is known as a club hair.

After catagen, the hair goes into a telogen phase. Telogen is the resting phase, which accounts for 10-15% of all hairs. It lasts for about 100 days for hairs on the scalp and much longer for hairs on the eyebrow, eyelash, arm and leg. During this phase the hair follicle is completely at rest and the club hair is completely formed. As compared with anagen hair, telogen hair is located higher in the skin and can be pulled out relatively easily. Pulling out a hair in this phase will reveal a solid, hard, dry, white material at the root. Normally, about 25-100 telogen hairs are shed each day.

In the normal scalp, approximately 80 to 90 percent of follicles are growing (anagen), about 5 to 10 percent are resting (telogen), and 1 to 3 percent are undergoing involution (catagen). Each day up to 75 hairs in telogen are shed from the scalp and about the same number of follicles enter anagen.

The term "alopecia" is a medical term for the absence or loss of hair including eyelashes, eyebrows, and scalp hair, as a result of illness, functional disorder, or hereditary disposition. For example, the term "Alopecia adnata" refers to underdevelopment of the eyelashes. Alopecia frequently occurs in patients undergoing treatment for cancer or suffering from other diseases, such as AIDS, where cell-killing, or cytotoxic, drugs are used.

Hair loss typically is categorized as scarring or nonscarring. Scarring alopecia, also known as "cicatricial alopecia", refers to a collection of hair loss disorders that may be diagnosed in up to 3% of hair loss patients. It occurs worldwide in otherwise healthy men and women of all ages. While there are many forms of scarring alopecia, the common theme is a potentially permanent and irreversible destruction of hair follicles and their replacement with scar tissue. Examples include bullous diseases, chemical alopecia, discoid lupus erythematosus, folliculitis (severe), lichen planopilaris, dissecting cellulitis, and tumors.

The term "nonscarring alopecia" refers to hair loss without permanent destruction of the hair follicle. Examples include anagen effluvium, androgenetic alopecia, chemical alopecia, folliculitis (mild), inherited disorders of the hair shaft, telogen effluvium, alopecia areata, and traumatic alopecia.

The term "anagen effluvium" refers to the hair loss associated with chemotherapeutic agents that cause immediate destruction and release of anagen hair.

The term "androgenic alopecia" refers to a gradual decrease of scalp hair density in adults with transformation of terminal to vellus hairs, which become lost as a result of familial increased susceptibility of hair follicles to androgen secretion following puberty. The most common form of androgenic alopecia is male pattern baldness. The most common form of androgenic alopecia in women is female pattern alopecia, a diffuse partial hair loss in the centroparietal area of the scalp, with preservation of the frontal and temporal hairlines. When it occurs in females, it is associated with other evidence of excessive androgen activity, such as hirsuitism.

The term "telogen effluvium" refers to a condition resulting from an abrupt shift of large numbers of anagen hairs to telogen hairs on the scalp, with a corresponding change in the ratio of anagen hair to telogen hair from the normal ratio of 90:10 to 70:30. This form of alopecia generally begins approximately 3 months after a major illness or other stress (e.g., surgery, parturition, rapid weight loss, nutritional deficiency, high fever, or hemorrhage) or hormonal derangement; it also has been reported after the initiation of treatment with certain medications.

The term "alopecia areata" refers to a common condition of undetermined etiology characterized by circumscribed, nonscarring, usually asymmetrical areas of baldness on the scalp, eyebrows, and beaded portion of the face. Hairy skin anywhere on the body may be affected. It is thought to be an autoimmune disease occurring on areas of the body (most commonly the scalp) where the person's immune system attacks hair follicles, thereby suppressing and arresting hair growth.

Those suffering from hair loss often experience embarrassment and the fear being ridiculed by others because they look different. Some may take to wearing oversized eyeglasses in an attempt to hide the absence of eyelashes and/or eyebrows. Loss of nasal cilia may render some more susceptible to respiratory illnesses.

Current therapies for hair loss are designed primarily for scalp applications. These include topical minoxidil (Rogain®), antiandrogen agents, including the androgen-receptor blockers sprionolactone, cyproterone acetate, and flutamide, and the 5α-reductase inhibitor finasteride (Propecia®, Merck & Co.), preparations of progresterone and/or estrogen, and hair transplantation.

Prostaglandins are a family of a group of lipid compounds that are derived enzymatically in the body from essential fatty acids. Every prostaglandin contains 20 carbon atoms, including a 5-carbon ring. Prostaglandins have a wide variety of effects, including, but not limited to, muscular constriction, mediating inflammation, calcium movement, hormone regulation and cell growth control. Prostaglandins act on a variety of cells, including vascular smooth muscle cells (causing constriction or dilation), platelets (causing aggregation or disaggregation), and spinal neurons (causing pain).

Scientists stumbled on the hair thickening properties of prostaglandin $F_{2\alpha}$ analogs while researching their use as an intraocular pressure (IOP)-lowering drug for use in patients with glaucoma and ocular hypertension. Prostaglandin $F_{2\alpha}$ analogs have the following general chemical structure wherein the dashed bonds represent a single or double bond which can be in the cis or trans configuration:

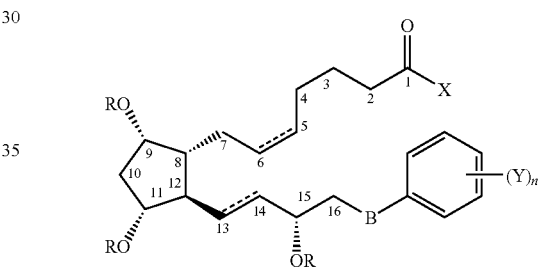

For example, latanoprost [(1R,2R,3R,5S)3,5-dihydroxy-2-[(3R)-3-hydroxy-5-phenylpentyl]cyclopentyl]-5-heptenoate], marketed by Pfizer as Xalatan® is a prostaglandin analog in which R is H, B is —CH$_2$—, n is 0, X is OCH(CH$_3$)$_2$, and the dashed bonds represent a double bond. See U.S. Pat. No. 6,262,105, issued to Johnstone. Although Johnstone reported the stimulating effect of this drug on eyebrow and eyelash hair growth and pigmentation, Latanoprost works poorly on eyelashes.

Another example, is bimatoprost (cyclopentane N-ethyl heptenamide-5-cis-2-(3α-hydroxy-5-phenyl-1-trans-pentenyl)-3,4-dihydroxy, [1$_\alpha$, 2$_\beta$, 3$_\alpha$, 5$_\alpha$], sold by Allergan, Inc. of Irvine, Calif. as Lumigan®, a 0.03% ophthalmic solution for treating glaucoma. Bimatoprost is a prostaglandin analog in which R is H, B is —CH$_2$—, n is 0, X is NHC$_2$H$_5$ and the dashed bonds represent a double bond (U.S. Published Application No. 2003/0147823). Bimatoprost, which also has been found effective to increase the growth of eyelashes when applied in the FDA approved manner, dissolves best for use on eyelashes but has negative side effects, such as, for example, redness and discoloration along the periocular skin; eye irritation; and foreign body sensation. In addition, bimatoprost has the highest incidence of hyperemia.

Another synthetic prostaglandin analog used for treatment of glaucoma is isopropyl (Z)-7-[(1R,2R,3R,5S)-3,5-dihydroxy-2-[(1E,3R)-3-hydroxy-4-[(α,α,α-trifluoro-m-tolyl)

oxy]-1-butenyl]cyclopentyl]-5-heptenoate, or Travaprost (TRAVATAN® Alcon), which is available as a 0.004% ophthalmic solution. Travoprost is a prostaglandin analog in which R is H, B is O, Y is $CF_3$, X is $OCH(CH_3)_2$, and the dashed bonds represent a double bond. Travaprost does not work well for eyelash growth, taking longer than other like products.

Therefore it is an object of the present invention to provide prostaglandin analogs that will promote appropriate hair growth when applied topically to subjects in need thereof without causing significant undesirable side effects.

SUMMARY OF THE INVENTION

The present invention relates to the formulation and delivery of prostaglandin analogs to treat an epithelial-related condition. In some embodiments, the compositions of the invention are used to stimulate hair growth. In some embodiments, the compositions of the invention are used to restore hair color to depigmented hair. According to one aspect, the present invention provides a topical composition for treating an epithelial-related condition, comprising (a) at least one compound of formula XI or a salt of formula XI:

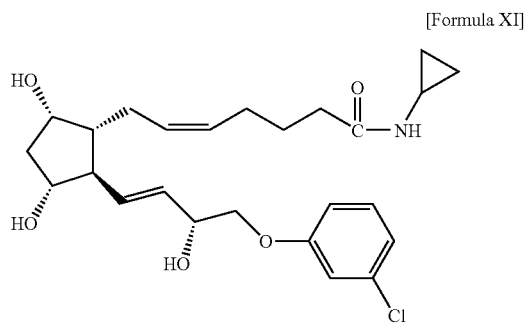

[Formula XI]

wherein the simple straight line represents a bond lying approximately in the surface plane; the wedge shaped bond is directed to the front of surface plane; and the hatched bond is directed in the back of the surface plane; and wherein the compound has optically active isomers whenever chiral centers are present; and (b) a carrier, whereby the composition stimulates hair growth on an epithelial surface to which the composition has been applied. According to one embodiment, the at least one compound of formula XI is (16-(3-chlorophenoxy)-17,18,19,20-tetranor $PGF_{2\alpha}$) cyclopropyl amide. According to another embodiment, the composition is an ophthalmic composition. According to another embodiment, the composition restores pigmentation to depigmented hair. According to another embodiment, the epithelial-related condition is alopecia. According to another embodiment, the epithelial surface onto which the composition is applied topically is an eyelid. According to another embodiment, the epithelial-related condition is alopecia of at least one eyelash. According to another embodiment, the epithelial surface onto which the composition is applied topically is a face. According to another embodiment, the condition is alopecia of at least one eyebrow. According to another embodiment, the epithelial surface onto which the composition is applied topically is above a lip. According to another embodiment, the compound of (a) is present in a pharmaceutically effective amount. According to another embodiment, the compound of (a) is present in a cosmetically effective amount. According to another embodiment, the compound of (a) is present in a cosmeceutically effective amount.

DETAILED DESCRIPTION OF THE INVENTION

The present invention relates to synthetic analogs of prostaglandin $F_{2\alpha}$.

"Aliphatic" as used herein, denotes a straight- or branched-chain arrangement of constituent carbon atoms, including, but not limited to paraffins (alkanes), which are saturated, olefins (alkenes or alkadienes), which are unsaturated, and acetylenes (alkynes), which contain a triple bond. In complex structures, the chains may be branched or cross-linked.

"Alkyl," as used herein, denotes a straight (unbranched) or branched univalent aliphatic group of about 1 to about 25 carbon atoms including, e.g., methyl, ethyl, propyl, isopropyl, decyl, undecyl, dodecyl, octadecyl, nonadecyl, eicosyl, heneicosyl, decosyl, tricosyl, tetracosyl, and pentacosyl, and the branched (non-straight-chained) isomers thereof, with multiple degrees of substitution being allowed. In some embodiments of the present invention, the prostaglandin analog has an alkyl of 1, 2, 3, 4, 5, 6, 7, 8, 9, 10, 11, or 12 carbon atoms.

"Alkenyl," as used herein, denotes a monovalent, straight (unbranched) or branched hydrocarbon chain having one or more double bonds therein where the double bond can be unconjugated or conjugated to another unsaturated group (e.g., a polyunsaturated alkenyl) and can be unsubstituted or substituted, with multiple degrees of substitution being allowed. For example, and without limitation, the alkenyl can be vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, decenyl, undecenyl, dodecenyl, heptadecenyl, octadecenyl, nonadecenyl, eicosenyl, heneicosenyl, docosenyl, tricosenyl, tetracisenyl, pentacosenyl, phytyl, the branched chain isomers thereof, and polyunsaturated alkenes including octadec-9,12,-dienyl, octadec-9,12, 15-trienyl, and eicos-5,8,11,14-tetraenyl.

As used herein, the term "aryl" refers to a benzene ring or to an optionally substituted benzene ring system fused to one or more optionally substituted benzene rings, with multiple degrees of substitution being allowed. Examples of aryl include, but are not limited to, phenyl, 2-napthyl, 1-naphthyl, 1-anthracenyl, and the like.

It should be understood that wherever the terms "alkyl" or "aryl" or either of their prefix roots appear in a name of a substituent, they are to be interpreted as including those limitations given above for alkyl and aryl.

As used herein, the terms "carbamates" or "urethanes" refer to a group of organic compounds sharing a common functional group having the general structure —NH(CO)O—.

As used herein, the terms "cycloalkyl" or "aliphatic cyclic" are used interchangeably to refer to an alicyclic hydrocarbon group optionally possessing one or more degrees of unsaturation, having from three to twelve carbon atoms, optionally substituted with substituents, with multiple degrees of substitution being allowed. "Cycloalkyl" includes, but is not limited to, cyclopropyl, cyclobutyl, cyclopentyl, cyclohexyl, cycloheptyl, cyclooctyl, and the like.

As used herein, the terms "heterocycle" and "heterocyclic" are used interchangeably to refer to a three to twelve-membered heterocyclic ring optionally possessing one or more degrees of unsaturation, containing one or more heteroatomic substitutions selected from —S—, —SO—, —SO$_2$—, —O—, or —N—, optionally substituted with substitutents, including, but not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring optionally may be fused to one or more of another "heterocyclic" ring(s). Examples of "heterocyclic" include, but are not limited to, pyrrole, furan, thiophene, imidazole, oxazole, thiazole, pyrazole, 3-pyrroline, pyrrolidine, pyridine, pyrimidine, purine, quinoline, isoquinoline, carbazole and the like.

The term C-linked heterocycle means a heterocycle that is bonded through a carbon atom, e.g. —$(CH_2)_n$-heterocycle where n is 1, 2 or 3 or —C<heterocycle where C< represents a carbon atom in a heterocycle ring. Similarly, R moieties that are N-linked heterocycles mean a heterocycle that is bonded through a heterocycle ring nitrogen atom, e.g. —N<heterocycle where N< represents a nitrogen atom in a heterocycle ring. A variable group such as an R moiety that is bonded to a Formula I compound can be a C-linked heterocycle or a N-linked heterocycle. These heterocycles include those listed below or described elsewhere herein.

Examples of heterocycles include by way of example and not limitation pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, .beta.-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at the nitrogen atom or position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or .beta.-carboline. Typically, nitrogen bonded heterocycles include 1-aziridyl, 1-azetedyl, 1-pyrrolyl, 1-imidazolyl, 1-pyrazolyl, and 1-piperidinyl optionally substituted structures such as and tautomers of any of these.

"Heteroaryl" means an aromatic ring or two or more fused rings that contain one or more aromatic rings where the ring or fused rings comprise 1, 2, 3 or more heteroatoms, usually oxygen (—O—), nitrogen (—NX—) or sulfur (—S—) where X is —H, a protecting group or optionally substituted alkyl. Examples are as described for heterocycle.

As used herein the term "isomer" refers to one of two or more molecules having the same number and kind of atoms and hence the same molecular weight, but differing in respect to the arrangement or configuration of the atoms. Generally, differences in compounds having identical molecular and chemical formulas but differing in the way their atoms are arranged three-dimensionally in space create optically active isomers or enantiomers. These enantiomers are called (D- (for dexorotatory, right-handed or +) or L- (levorotatory, left-handed, or −) for the direction in which they rotate plane-polarized light. A mixture of equal parts of the optical forms of a compound is known as a racemic mixture or racemate. A racemic mixture is optically inactive, i.e., it consists of equal parts of D- and L-enantiomers. The alpha-carbon atom of all amino acids (with the exception of glycine) is a center of asymmetry. This asymmetry likewise creates isomers having differences in the spatial orientation of their atoms in space. Although amino acids are optically active such that the sign and magnitude of the optical rotation of an amino acid is a function of the pH of the solution in which it is measured and of the nature of its side chain, the D or L designation here does not refer to optical activity. Instead, it indicates absolute configurations relative to those of the related compound glyceraldehyde.

The term "O-linked moiety" means a moiety that is bonded through an oxygen atom. Thus, when an R group is an O-linked moiety, that R is bonded through oxygen and it can thus be an ether, an ester (e.g., —O—C(O)-optionally substituted alkyl), a carbonate or a carbamate (e.g., —O—C(O)—NH$_2$ or —O—C(O)—NH-optionally substituted alkyl). Similarly, the term "S-linked moiety" means a moiety that is bonded through a sulfur atom. Thus, when an R group is an S-linked moiety, that R is bonded through sulfur and it can thus be a thioether (e.g., —S-optionally substituted alkyl), a thioester (—S—C(O)-optionally substituted alkyl) or a disulfide (e.g., —S—S-optionally substituted alkyl). The term "N-linked moiety" means a moiety that is bonded through a nitrogen atom. Thus, when an R group is an N-linked moiety, the R group is bonded through nitrogen and one or more of these can thus be an N-linked amino acid such as —NH—CH$_2$—COOH, a carbamate such as —NH—C(O)—O-optionally substituted alkyl, an amine such as —NH-optionally substituted alkyl, an amide such as —NH—C(O)-optionally substituted alkyl or —N$_3$. The term "C-linked moiety" means a moiety that is bonded through a carbon atom. When one or more R group is bonded through carbon, one or more of these can thus be -optionally substituted alkyl such as —CH$_2$—CH$_2$—O—CH$_3$, —C(O)-optionally substituted alkyl hydroxyalkyl, mercaptoalkyl, aminoalkyl or =CH-optionally substituted alkyl.

As used herein, the term "ethoxy" refers to the substituent —O—CH$_2$CH$_3$.

As used herein, the term "methoxy" refers to the substituent —O—CH$_3$. As used herein, the term "optionally" means that the subsequently described event(s) may or may not occur, and includes both event(s) which occur and events that do not occur.

As used herein the term "carbohydrate" refers to aldehyde or ketone compounds with multiple hydroxyl groups. The term "monosaccharide" or "simple sugar" refers to a carbohydrate that does not hydrolyze. Examples of monosaccharides include glucose (dextrose), fructose, galactose, xylose and ribose. Monosaccharides are the building blocks of disaccharides like sucrose (common sugar) and polysaccharides (such as cellulose and starch). Further, each carbon atom that supports a hydroxyl group (except for the first and last) is chiral, giving rise to a number of isomeric forms all with the same chemical formula.

The term "configuration" as used herein refers to the three-dimensional shape of a molecule. This shape is dependent on the preferred spatial orientation of covalent bonds to atoms having two or more bonding partners. In order to represent three-dimensional configurations on a two-dimensional surface, perspective drawings in which the direction of a bond is specified by the line connecting the bonded atoms are used. Formula XIII shows an illustrative perspective drawing:

[Formula XIII]

In formula XIII, the focus of configuration is a carbon (C) atom so the lines specifying bond directions will originate there. A simple straight line represents a bond lying approximately in the surface plane, as shown by the two bonds to substituent "A." A wedge shaped bond is directed in front of this plane (thick end toward the viewer), as shown by the bond to substituent "B." A hatched bond is directed in back of the plane (away from the viewer), as shown by the bond to substituent "D." A dashed bond represents a single or double bond which can be in the cis or trans configuration.

The prostaglandin $F_{2\alpha}$ analog of the present invention is a compound of Formula (I) or a salt of Formula (I):

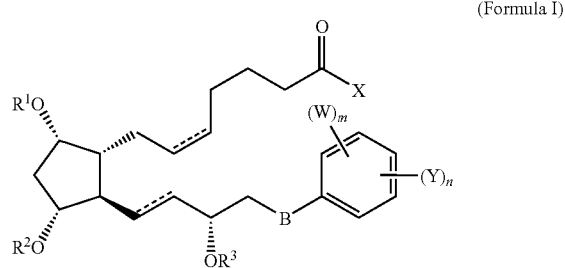

(Formula I)

wherein $R^1$, $R^2$ and $R^3$ each independently is H, $C_1$-$C_6$ alkyl, a phosphate group, a monosaccharide, a disaccharide or a polysaccharide;

the simple straight line represents a bond lying approximately in the surface plane; the dashed bonds represent a single or double bond which can be in the cis or trans configuration, wherein there is at least one double bond; the wedge shaped bond is directed to the front of surface plane (thick end toward the viewer); and the hatched bond is directed in the back of the surface plane (away from the viewer);

B is —O—, —S—, —SO—, —S(O$_2$)—, —(CH$_2$)$_a$—, where a is 0, 1, or 2, or —NR$^6$—, where R$^6$ is H or $C_1$-$C_6$ alkyl;

X is —NHR$^4$, where R$^4$ is OH, alkyl, alkenyl, aryl, cycloalkyl, alkylcycloalkyl, cycloalkenyl, a heterocycle, or a carbamate; X is a cyclic substituent in which nitrogen is part of the ring, represented as —N(R$^4$)$_2$, wherein (R$^4$)$_2$ is —(CH$_2$)$_k$—where k is 2 to 10; or X is —OR$^5$, where R$^5$ is H, alkyl, alkenyl, aryl, cycloalkyl, alkylcycloalkyl, a heterocycle or a carbamate;

$W_m$, wherein m is 0 or greater, is such that any of the carbons on the aryl ring may be replaced by at least two heteroatoms selected from the group consisting of N, S and O;

n is a whole number between 0 and 5; and

Y is one or more $C_1$-$C_5$ alkyl groups, $C_1$-$C_5$ haloalkyl groups, $C_1$-$C_5$ alkoxy groups, $C_1$-$C_5$ haloalkoxy groups, $C_1$-$C_5$ aliphatic acylamino groups, nitro groups, halogen atoms, an aromatic heterocyclic group having 5-6 ring atoms and having at least one heteroatom, the heteroatom being N, O, or S; a $C_3$-$C_7$ cycloalkane or a $C_3$-$C_7$ cycloalkene optionally substituted with $C_1$-$C_5$ alkyl groups.

In preferred embodiments,

X is

NHR$^4$, wherein R$^4$ is OH, alkenyl, aryl, cycloalkyl, alkylcycloalkyl, cycloalkenyl, a heterocycle, or a carbamate;

a cyclic substituent in which nitrogen is part of the ring, represented as —N(R$^4$)$_2$, wherein (R$^4$)$_2$ is —(CH$_2$)$_k$— where k is 2 to 10; or OR$^5$, where R$^5$ is alkenyl, aryl, alkylcycloalkyl, a heterocycle or a carbamate; and $R^1$, $R^2$ and $R^3$ each independently is H, $C_1$-$C_6$ alkyl, a phosphate group, a monosaccharide, a disaccharide or a polysaccharide;

the simple straight line represents a bond lying approximately in the surface plane; the dashed bonds represent a single or double bond which can be in the cis or trans configuration, wherein there is at least one double bond; the wedge shaped bond is directed to the front of surface plane (thick end toward the viewer); and the hatched bond is directed in the back of the surface plane (away from the viewer)

B is —O—, —S—, —(CH$_2$)$_a$—, where a is 0, 1, or 2, or —NR$^6$—, where R$^6$ is H or $C_1$-$C_6$ alkyl; —SO— or (SO)$_2$, such that optically active isomers are included whenever chiral centers are present;

$W_m$ wherein m is 0 or greater, is such that any of the carbons on the aryl ring may be replaced by at least two heteroatoms selected from the group consisting of N, S and O;

n is a whole number between 0 and 5; and

Y is one or more $C_1$-$C_5$ alkyl groups, $C_1$-$C_5$ haloalkyl groups, $C_1$-$C_5$ alkoxy groups, $C_1$-$C_5$ haloalkoxy groups, $C_1$-$C_5$ aliphatic acylamino groups, nitro groups, halogen atoms, an aromatic heterocyclic group having 5-6 ring atoms and having at least one heteroatom, the heteroatom being N, O, or S; a $C_3$-$C_7$ cycloalkane or a $C_3$-$C_7$ cycloalkene optionally substituted with $C_1$-$C_5$ alkyl groups.

In some embodiments, when X is NHR$^4$, wherein R$^4$ is OH, alkenyl, aryl, cycloalkyl, alkylcycloalkyl, cycloalkenyl, a heterocycle, or a carbamate, $R^1$, $R^2$ and $R^3$ each independently is H, B is —(CH$_2$)$_a$—, where a is 0, 1, or 2, and m and n are 0. In some embodiments, when X is NHR$^4$ and R$^4$ is OH, alkenyl, aryl, cycloalkyl, alkylcycloalkyl, cycloalkenyl, a heterocycle, or a carbamate, $R^1$, $R^2$ and $R^3$ each independently is H, B is —O—, and m and n are 0. In some embodiments, when X is NHR$^4$ and R$^4$ is OH, alkenyl, aryl, cycloalkyl, alkylcycloalkyl, cycloalkenyl, a heterocycle, or a carbamate, $R^1$, $R^2$ and R$^3$ each independently is H, B is —S—, and m and n are 0. In some embodiments, when X is NHR⁴ and R⁴ is OH, alkenyl, aryl, cycloalkyl, alkylcycloalkyl, cycloalkenyl, a heterocycle, or a carbamate, R¹, R² and R³ each independently is H, B is —SO—, and m and n are 0. In some embodiments, when X is NHR⁴ and R⁴ is OH, alkenyl, aryl, cycloalkyl, alkylcycloalkyl, cycloalkenyl, a heterocycle, or a carbamate, R¹, R² and R³ each independently is H, B is —S(O)₂—, and m and n are 0. In some embodiments, when X is NHR⁴ and R⁴ is OH, alkenyl, aryl, cycloalkyl, alkylcycloalkyl, cycloalkenyl, a heterocycle, or a carbamate, R¹, R² and R³ each independently is H, B is —NR⁶-where R⁶ is H or C₁-C₆ alkyl and m and n are 0.

In some embodiments, when X is a cyclic substituent in which nitrogen is part of the ring, represented as —N(R⁴)₂ and (R⁴)₂ is —(CH₂)ₖ- where k is 2 to 10, R¹, R² and R³ each independently is H, B is —(CH₂)ₐ—, where a is 0, 1, or 2, and m and n are 0. In some embodiments, when X is —N(R⁴)₂ and (R⁴)₂ is —(CH₂)ₖ- where k is 2 to 10, R¹, R² and R³ each independently is H, B is —O—, and m and n are 0. In some embodiments, when X is —N(R⁴)₂ and (R⁴)₂ is —(CH₂)ₖ- where k is 2 to 10, R¹, R² and R³ each independently is H, B is —S—, and m and n are 0. In some embodiments, when X is —N(R⁴)₂ and (R⁴)₂ is —(CH₂)ₖ- where k is 2 to 10, R¹, R² and R³ each independently is H, B is —SO—, and m and n are 0. In some embodiments, when X is —N(R⁴)₂ and (R⁴)₂ is —(CH₂)ₖ- where k is 2 to 10, R¹, R² and R³ each independently is H, B is —SO₂—, and m and n are 0. In some embodiments, when X is —N(R⁴)₂ and (R⁴)₂ is —(CH₂)ₖ- where k is 2 to 10, R¹, R² and R³ each independently is H, B is —NR⁶-where R⁶ is H or C₁-C₆ alkyl and m and n are 0.

In some embodiments, when X is OR⁵, R⁵ is alkenyl, aryl, alkylcycloalkyl, a heterocycle or a carbamate. In some such embodiments, R¹, R² and R³ each independently is H, B is —(CH₂)ₐ—, where a is 0, 1, or 2, and m and n are 0. In some such embodiments, R¹, R² and R³ each independently is H, B is —O—, and m and n are 0. In some such embodiments, R¹, R² and R³ each independently is H, B is —S—, and m and n are 0. In some such embodiments, R¹, R² and R³ each independently is H, B is —SO—, and m and n are 0. In some such embodiments, R¹, R² and R³ each independently is H, B is —SO₂—, and m and n are 0. In some embodiments, B is —NR⁶-where R⁶ is H or C₁-C₆ alkyl and m and n are 0.

In one embodiment, R¹, R², and R³ are H, X is a nitrogen-linked cyclopropyl group, B is —CH₂—, a is 1, and both m and n are 0. This compound of Formula I is 17 phenyl trinor PGF₂α cyclopropylamide, which has the structure:

(Formula II)

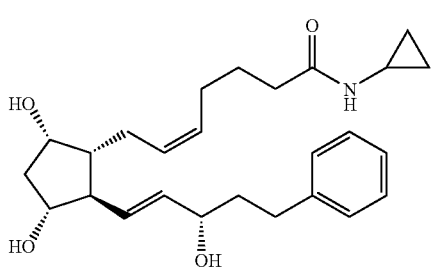

wherein the simple straight line represents a bond lying approximately in the surface plane; the wedge shaped bond is directed to the front of surface plane; and the hatched bond is directed in the back of the surface plane.

In another embodiment, R¹, R², and R³ are H, X is a nitrogen-linked methyl cyclopropyl group, B is —CH₂—, a is 1, and both m and n are 0. This compound is 17 phenyl trinor PGF₂α cyclopropyl methyl amide, which has the structure:

(Formula III)

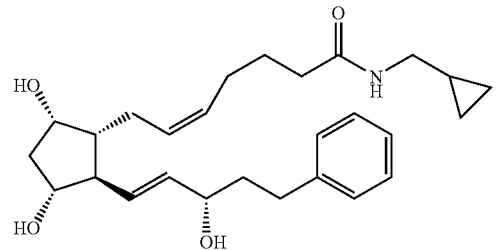

wherein the simple straight line represents a bond lying approximately in the surface plane; the wedge shaped bond is directed to the front of surface plane; and the hatched bond is directed in the back of the surface plane.

In yet another embodiment, R¹ is a phosphate group, R² is H, R³ is H, B is O, m and n are 0 and X is an oxygen-linked cyclopropyl group. This compound of Formula I has the structure:

(Formula IV)

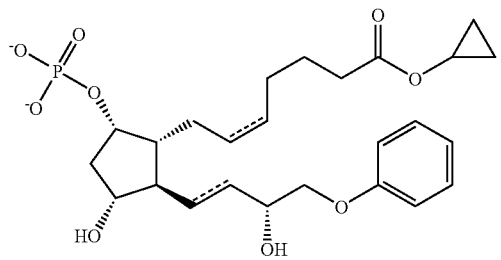

wherein the simple straight line represents a bond lying approximately in the surface plane; the dashed bonds represent a single or double bond which can be in the cis or trans configuration, wherein there is at least one double bond; the wedge shaped bond is directed to the front of surface plane; and the hatched bond is directed in the back of the surface plane.

In another embodiment, R¹, R², and R³ are each H, X is a nitrogen-linked cyclopropyl group, B is —O— and m and n are 0. This compound of Formula I has the structure:

(Formula V)

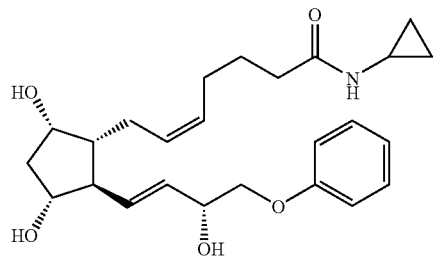

wherein the simple straight line represents a bond lying approximately in the surface plane; the wedge shaped bond is directed to the front of surface plane; and the hatched bond is directed in the back of the surface plane. This compound is 16-phenoxy tetranor PGF₂α cyclopropyl amide.

In another embodiment, R¹, R², and R³ are each H, X is a nitrogen-linked methyl cyclopropyl group, B is —O— and m and n are 0. This compound is 16-phenoxy tetranor PGF₂α cyclopropyl methyl amide, which has the structure:

(Formula VI)

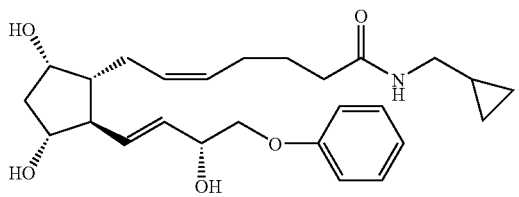

wherein the simple straight line represents a bond lying approximately in the surface plane; the wedge shaped bond is directed to the front of surface plane; and the hatched bond is directed in the back of the surface plane.

In another embodiment, $R^1$, $R^2$, and $R^3$ are each H, X is a nitrogen-linked cyclopropyl group, B is $CH_2$ where a is 1, and n is 0 and m is 2. This compound of Formula I has the structure:

(Formula VII)

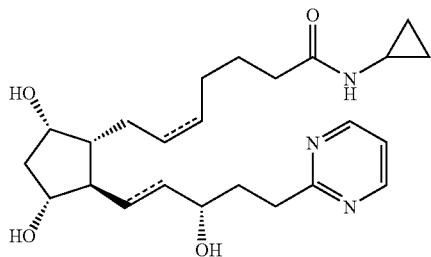

wherein the simple straight line represents a bond lying approximately in the surface plane; the dashed bonds represent a single or double bond which can be in the cis or trans configuration, wherein there is at least one double bond; the wedge shaped bond is directed to the front of surface plane; and the hatched bond is directed in the back of the surface plane.

In another embodiment, $R^1$ is a phosphate group, $R^2$ is H, $R^3$ is H, B is SO, m and n are 0 and X is an oxygen-linked cyclopropyl group. This compound of Formula I has the structure:

(Formula VIII)

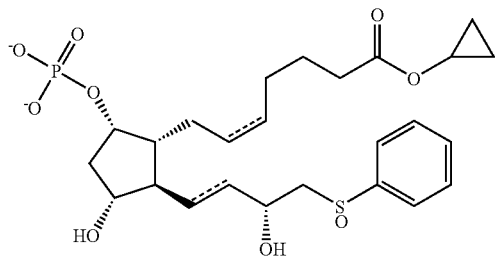

wherein the simple straight line represents a bond lying approximately in the surface plane; the dashed bonds represent a single or double bond which can be in the cis or trans configuration, wherein there is at least one double bond; the wedge shaped bond is directed to the front of surface plane; and the hatched bond is directed in the back of the surface plane.

In yet another embodiment, $R^1$ is a monosaccharide (e.g., glucose), $R^2$ and $R^3$ are H, X is a nitrogen-linked ethyl group; B is —$CH_2$ where a is 1, and m and n are 0. This compound of Formula I has the structure:

(Formula IX)

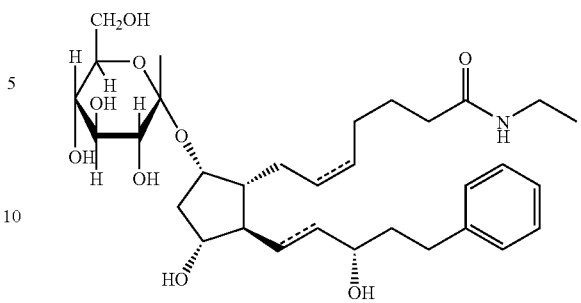

wherein the simple straight line represents a bond lying approximately in the surface plane; the dashed bonds represent a single or double bond which can be in the cis or trans configuration, wherein there is at least one double bond; the wedge shaped bond is directed to the front of surface plane; and the hatched bond is directed in the back of the surface plane.

In yet another embodiment, $R^1$ is a monosaccharide (e.g., glucose), $R^2$ and $R^3$ are H, X is a nitrogen-linked ethyl group; B is —$CH_2$ where a is 1, n is 2, and Y is a cyclopropyl group linked to a nitrogen heteroatom. This compound of Formula I has the structure:

(Formula X)

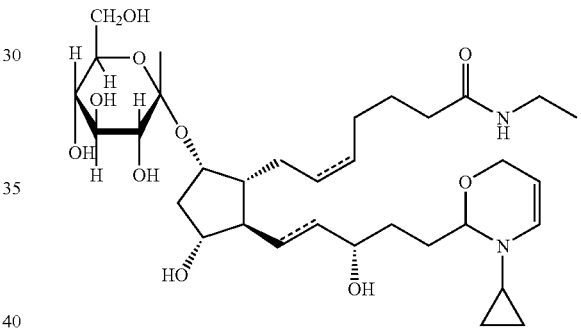

wherein the simple straight line represents a bond lying approximately in the surface plane; the dashed bonds represent a single or double bond which can be in the cis or trans configuration, wherein there is at least one double bond; the wedge shaped bond is directed to the front of surface plane; and the hatched bond is directed in the back of the surface plane.

In another embodiment, $R^1$, $R^2$ and $R^3$ each are —OH; X is $NHR^4$, where $R^4$ is cyclopropyl; B is —O; m=0; Y is Cl; and n=1. This compound of Formula I has the structure:

(Formula XI)

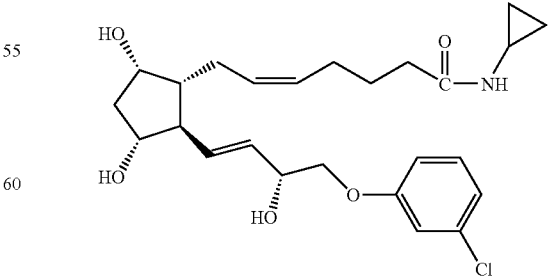

wherein the simple straight line represents a bond lying approximately in the surface plane; the wedge shaped bond is directed to the front of surface plane; and the hatched bond is directed in the back of the surface plane. This compound is (16-(3-chlorophenoxy)-17,18,19,20-tetranor $PGF_{2\alpha}$) cyclopropyl amide.

In another embodiment, $R^1$, $R^2$ and $R^3$ each are —OH; X is $NHR^4$, where $R^4$ is cyclopropyl methyl amide; B is —O; m=0; Y is Cl; and n=1. This compound of Formula I has the structure:

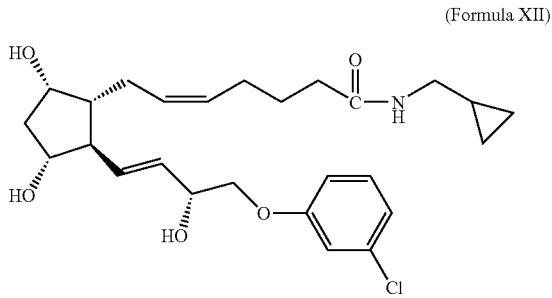

(Formula XII)

wherein the simple straight line represents a bond lying approximately in the surface plane; the wedge shaped bond is directed to the front of surface plane; and the hatched bond is directed in the back of the surface plane. This compound is (16-(3-chlorophenoxy)-17,18,19,20-tetranor $PGF_{2\alpha}$) cyclopropyl methyl amide. The compounds of the present invention can be formulated into pharmaceutical compositions. As used herein, "pharmaceutically acceptable salts" include, but are not limited to, those formed with free amino groups such as those derived from hydrochloric, phosphoric, sulfuric, acetic, oxalic, tartaric acids, etc., and those formed with free carboxyl groups, including, but not limited to, those derived from sodium, potassium, ammonium, calcium, ferric hydroxides, isopropylamine, triethylamine, 2-ethylamino ethanol, histidine, procaine, and the like.

The compounds of the present invention may be used in methods to treat an epithelial-related condition, the method comprising the steps (a) preparing at least one compound of the present invention; (b) formulating a composition with the at least one compound; and (c) administering the composition to a subject in need thereof.

The present invention provides topical compositions for treating an epithelial-related condition comprising hair loss in a subject in need of treatment thereof, including a human, that includes a compound of the invention and a carrier.

The phrase "epithelia" or "epithelial" or "epithelial tissues" as used herein is meant to include skin and mucosal membranes. Thus, the present invention offers compositions useful for treating a condition of the skin or a mucosal membrane, such as, but not limited to, that of a nose, an eye, a face, lip, and a scalp.

The term "topical" refers to administration of an inventive composition at, or immediately beneath, the point of application.

The phrase "topically applying" describes application onto one or more surfaces(s) including epithelial surfaces. "Topically applying" refers to direct application to the area of the surface to be affected. The composition may be applied by pouring, dropping, or spraying, if a liquid; rubbing on, if an ointment, lotion, cream, gel, or the like; dusting, if a powder; spraying, if a liquid or aerosol composition; or by any other appropriate means.

In another embodiment, the present invention provides a topical pharmaceutical composition for treating an epithelial-related condition comprising hair loss in a subject, including a human, in need of treatment thereof that includes at least one compound of the invention and a carrier.

In a further embodiment, the present invention provides a topical cosmetic composition for treating an epithelial-related condition comprising hair loss in a subject, including a human, in need of treatment thereof that includes at least one compound of the invention and a carrier.

In another embodiment, provided herein is a method of treating an epithelial-related condition comprising hair loss, the method including the step of topically applying onto an epithelial surface of a mammal, including a human, in need thereof a pharmaceutically effective amount of a composition that includes at least one compound of the invention and a carrier.

In a further embodiment, the invention provides a method of treating an epithelial-related condition comprising hair loss, the method including the step of topically applying onto a surface of a subject, including a human, in need thereof a cosmetically effective amount of a composition that includes at least one compound of the present invention and a carrier.

In a further embodiment, the invention provides a method of preparing a topical composition, the method including the step of admixing at least one compound of the present invention and a carrier.

The inventors have recognized that inventive compositions containing the compounds of the invention can be used effectively in topical applications to treat cosmetic conditions. These inventive compositions do not exhibit systemic effects when topically applied.

The compositions of the present invention may be usefully employed in cosmetic, cosmeceutical and general skincare compositions as well as in pharmaceutical compositions.

In one embodiment, the composition of the invention is a pharmaceutical composition. As used herein, a "pharmaceutical composition" refers to a composition that is employed to prevent, reduce in intensity, cure or otherwise treat a target condition.

In another embodiment, the composition of the invention is a cosmetic composition. As used herein a "cosmetic composition" refers to a composition that is intended to be rubbed, poured, sprinkled, or sprayed on, introduced into, or otherwise applied to a subject or any part thereof for cleansing, beautifying, promoting attractiveness, or altering the appearance, or an article intended for use as a component of any such article, except that such term does not include soap.

In another embodiment, the composition of the invention is a cosmeceutical composition. As used herein the term "cosmeceutical composition" refers to a composition that is employed as both a cosmetic composition and as a pharmaceutical composition.

In another embodiment, the composition of the invention is a cosmetic composition that restores hair pigmentation to depigmented hair.

Hair color is the result of pigmentation of the hair. Stem cells at the base of hair follicles are responsible for producing melanocytes, the cells that produce and store pigment in hair and skin. At some point in the aging process, these cells make less and less pigment, until the hair has very little pigment. White hair has no pigment, while gray hair has some pigment.

The graying process usually is gradual. However, it has been noted that tobacco smoking may cause premature graying. Additionally, there are a number of medical conditions that affect hair color. For example, albinism is a genetic abnormality in which no pigment is found in human hair, eyes or skin. Vitiligo is the patchy loss of hair and skin color that may occur as the result of an autoimmune disease. Malnutrition, which is reversible with proper nutrition, is known to cause hair to become lighter, thinner, and more brittle. Patients suffering from Werner syndrome, a rare autosomal recessive disorder that resembles accelerated aging, develop many of the changes associated with aging as young adults, including the graying and loss of hair. Pernicious anemia due to $B_{12}$ deficiency also can cause premature graying.

In another aspect of the present invention, the composition of the present invention includes a carrier. As used herein "carrier" describes a material that does not cause significant irritation to an organism and does not abrogate the biological activity and properties of the compound of the composition of the present invention. Carriers must be of sufficiently high purity and of sufficiently low toxicity to render them suitable for administration to the mammal being treated. The carrier can be inert, or it can possess pharmaceutical benefits, cosmetic benefits or both.

Some non-limiting representative examples of carriers include moisturizing agents or humectants, pH adjusting agents, hair conditioning agents, chelating agents, preservatives, emulsifiers, thickeners, solubilizing agents, penetration enhancers, anti-irritants, colorants and surfactants.

As used herein a "moisturizing agent" is a substance that adds or restores moisture to the skin. Representative examples of moisturizing or humectant agents that are usable in the present invention include, without limitation, guanidine, glycolic acid and glycolate salts (e.g. ammonium salt and quaternary alkyl ammonium salt), aloe vera in any of its variety of forms (e.g., aloe vera gel), allantoin, urazole, polyhydroxy alcohols such as sorbitol, glycerol, hexanetriol, propylene glycol, butylene glycol, hexylene glycol and the like, polyethylene glycols, sugars and starches, sugar and starch derivatives (e.g., alkoxylated glucose), hyaluronic acid, lactamide monoethanolamine, acetamide monoethanolamine and any combination thereof.

As is widely recognized in the art, since the pH of the skin is 5.5, compositions for topical skin application (to avoid irritation) can have a pH value of between about pH 4.0 and about pH 7.0, or between about pH 5.0 and about pH 6.0, or about pH 5.5 or substantially pH 5.5. Hence, a pH adjusting composition is typically added to bring the pH of the composition to the desired value. The compositions of the present invention therefore may be formulated to have a pH value of about 7.2. Suitable pH adjusting agents include, for example, but are not limited to, one or more adipic acids, glycines, citric acids, calcium hydroxides, magnesium aluminometasilicates, buffers or any combinations thereof.

Suitable hair conditioning agents that can be used in the context of the present invention include, for example, one or more collagens, cationic surfactants, modified silicones, proteins, keratins, dimethicone polyols, quaternary ammonium compounds, halogenated quaternary ammonium compounds, alkoxylated carboxylic acids, alkoxylated alcohols, alkoxylated amides, sorbitan derivatives, esters, polymeric ethers, glyceryl esters, or any combinations thereof.

Hair stimulating agents may be added to the compositions of the present invention. For example Procapil® (FR 2 791 684 and WO0058347) promotes the visible appearance of thicker and fuller hair and prevents premature hair thinning and hair loss by boosting the synthesis of components at the epidermal junction where the hair anchors to the skin, which helps to anchor the hair follicles more firmly to the scalp. U.S. Pat. No. 6,861,077 describes methods to protect keratinous fibers from extrinsic damages comprising application of compositions comprising at least one plant extract. For example, a plant extract composed of purified glycoproteins obtained from white potatoes (*Solanum tuberosum* L.) is commercially available from SEDERMA, Inc. (France) as Dermolectine® and Capilectine®. ANCRIN® (Sederma), a hydroglycolic solution containing octylbutyrate and glutamine peptide, reduces hair loss by supplying a vegetable substrate to transglutaminases, a group of enzymes known to increase protein reticulation in the scalp and help anchor the hair to the scalp. Capisome™ (Sederma) is a liposome that comprises homotaurine (3-aminopropane sulfonic acid), a bacterial filtrate of biotechnological origin from enterobacteria that contains high levels of peptides and the sulfur-containing amino acids methionine and cysteine; and marine sulfopolysaccharides. (See U.S. Pat. No. 6,376,557, incorporated herein by reference). Capigen™ (Sederma), is a complex that comprises homotaurine (3-aminopropane sulfonic acid), a bacterial filtrate obtained from a strain of microorganisms cultured in a medium comprising selected peptides, with the filtrate containing high levels of peptides, and a sulfomuycopolysaccharide of marine origin, which is a complex of sulfated polysaccharides that are soluble in water and are found in the connective tissue and synovial fluids. Follicusan® (Chemlishes Laboratorium Dr. Kurt Richter GmbH), is composed of a fraction derived from milk, ethyl pantenol, inositol and sulfur-containing amino acids (N-acetylcysteine and N-acetyl methionine in an aqueous alcoholic medium. Anageline® (Silab) contains an extract from white sweet lupine. Cprillisil (Exsymol S.A.M. of Monaco) is a 20% solution of dimethylsilanediol salicilate in butylenes glycol with triethanolamine. Mahanimba is an extract of the flowers and inflorescence of the neem tree (*Melia azadirachta*) and contains carotinoids, amino acids, phytosterols, mucins, polyacetylenes, and ses quiterpenes. Malkagni is an extract of the seeds, leaves and flowers of the intellect tree (*Celastrus paniculata*) and contains tannins, mineral salts, saponins, and iridic glycosides. Fitopur B is a complex available from Sederma, Inc., and comprises extracts of three plants: buchu (*Buc hu barosma*), henna (*Lawsonia inermis*), and venus hair (*Adiantum capillus-veneris*). The essential oil of buchu contains the terpenic oil diosphenol and sulfur compounds. The leaves of henna contain flavonic pigments, including luteoline and laxanthones, principally lawsone. Venus hair is a small fir native to the south of France; it has diuretic and emollient activity. Peptide-copper complexes containing dipeptides or tripeptides chelated to copper stimulate hair growth (see U.S. Pat. No. 5,538,945 and U.S. Pat. No. 6,017,888, incorporated herein by reference). Hormone replacement therapy (HRT), including administration of micronized progesterone pills and creams and estrogen pills and creams, is used to treat androgenetic alopecia for women. Other such agents are known by persons of skill in the art.

Chelating agents are optionally added to the compositions of the present invention so as to enhance the preservative or preservative system. Chelating agents that are mild agents, such as, for example, ethylenediaminetetraacetic acid (EDTA), EDTA derivatives, or any combination thereof, are particularly useful.

Suitable preservatives for use in the compositions of the present composition include, without limitation, one or more alkanols, disodium EDTA (ethylenediamine tetraacetate), EDTA salts, EDTA fatty acid conjugates, isothiazolinone, parabens such as methylparaben and propylparaben, propylene glycols, sorbates, urea derivatives such as diazolindinyl urea, or any combinations thereof.

"Emulsifiers" as used herein promote the formation and stabilization of an emulsion. Suitable emulsifiers may be natural materials, finely divided solids, or synthetic materials. Natural emulsifying agents may be derived from either animal or vegetable sources. Those from animal sources include gelatin, egg yolk, casein, wool fat, or cholesterol. Those from vegetable sources include acacia, tragacanth, chondrus, or pectin. Vegetable sources specifically from cellulose derivatives include methyl cellulose and carboxymethyl cellulose to increase the viscosity. Finely divided emulsifiers include bentonite, magnesium hydroxide, aluminum hydroxide, or magnesium trisylicate. Synthetic agents include anionic, cationic or nonionic agents. Particularly useful are sodium lauryl sulfate, benzalkonium chloride or polyethylene glycol 400 monostearate, or any combinations thereof.

"Thickeners" as used herein refer to agents that make the composition of the present invention dense or viscous in consistency. Suitable thickeners that can be used in the context of the present invention include, for example, non-ionic water-soluble polymers such as hydroxyethylcellulose (commercially available under the Trademark Natrosol® 250 or 350), cationic water-soluble polymers such as Polyquat 37 (commercially available under the Trademark Synthalen® CN), fatty alcohols, fatty acids, anionic polymers, and their alkali salts and mixtures thereof.

As used herein, the term "solubilizing agents" refers to those substances that enable solutes to dissolve. Representative examples of solubilizing agents that are usable in the context of the present invention include, without limitation, complex-forming solubilizers such as citric acid, ethylenediamine-tetraacetate, sodium meta-phosphate, succinic acid, urea, cyclodextrin, polyvinylpyrrolidone, diethylammonium-ortho-benzoate, and micelle-forming solubilizers such as TWEEN® and spans, e.g., TWEEN 80®. Other solubilizers that are usable for the compositions of the present invention are, for example, polyoxyethylene sorbitan fatty acid ester, polyoxyethylene n-alkyl ethers, n-alkyl amine n-oxides, polyoxamers, organic solvents, such as acetone, phospholipids and cyclodextrins.

The term "penetration enhancer" as used herein refers to an agent known to accelerate the delivery of a substance through the skin. Suitable penetration enhancers usable in the present invention include, but are not limited to, a vegetable oil. Such oils include, for example, safflower oil, cottonseed oil and corn oil.

Additional thickeners, penetration enhancers and other adjuvants may generally be found in Remington's Pharmaceutical Sciences, 18th or 19th editions, published by the Mack Publishing Company of Easton, Pa. which is incorporated herein by reference.

As used herein, an "anti-irritant" refers to an agent that prevents or reduces soreness, roughness, or inflammation of a bodily part. Suitable anti-irritants that can be used in the context of the present invention include, for example, steroidal and non steroidal anti-inflammatory agents or other materials such as aloe vera, chamomile, alpha-bisabolol, cola nitida extract, green tea extract, tea tree oil, licorice extract, allantoin, caffeine or other xanthines, glycyrrhizic acid and its derivatives.

The presently known anti-irritants can be divided into water-soluble anti-irritants and water-insoluble anti-irritants. Representative examples of such compositions are described, for example, in U.S. Pat. No. 5,482,710 which is herein incorporated by reference.

Colorants may also be used in the compositions of the invention. Colorants include pigments or dyes or a combination thereof as the cosmetic benefit requires. Preferred pigments include, but are not limited to, iron oxides, and titanium oxides. Suitable dyes include FD&C approved colorants, D&C approved colorants, and those approved for use in Europe and Japan (see Marmion, D. M., Handbook of US Colorants for Food, Drugs, Cosmetics, and Medical Devices, 3rd ed, 1991 herein incorporated by reference). The term "color" as used herein refers to the quality of an object or substance with respect to light reflected or absorbed by the object or substance. The three characteristics of color are hue, intensity, and value. "Hue" refers to a gradation, tint, or variety of a color. "Intensity", "chroma", and "saturation" are used interchangeably to refer to the strength or sharpness of a color. A color is full in intensity only when pure and unmixed. "Value" refers to a degree of lightness or darkness in a color.

The term "surfactants" as used herein refers to surface-active substances, such as a detergent. Suitable surfactants for use with the inventive compositions include, but are not limited to, sarcosinates, glutamates, sodium alkyl sulfates, ammonium alkyl sulfates, sodium alkyleth sulfates, ammonium alkyleth sulfates, ammonium laureth-n-sulfates, sodium laureth-n-sulfates, isothionates, glycerylether sulfonates, sulfosuccinates and combinations thereof. More preferably, the anionic surfactant is selected from the group consisting of sodium lauroyl sarcosinate, monosodium lauroyl glutamate, sodium alkyl sulfates, ammonium alkyl sulfates, sodium alkyleth sulfates, ammonium alkyleth sulfates, and combinations thereof.

In some embodiments, a pharmaceutically acceptable carrier is included in the composition. As used herein the term "pharmaceutically acceptable carrier" refers to any substantially non-toxic carrier conventionally useable for topical administration of pharmaceuticals in which the compound will remain stable and bioavailable when applied directly to skin or mucosal surfaces.

In another embodiment, the compositions of the present invention include a cosmetically acceptable carrier. As used herein the phrase "cosmetically acceptable carrier" refers to a substantially non-toxic carrier, conventionally useable for the topical administration of cosmetics, with which compounds will remain stable and bioavailable. It will be understood that cosmetically acceptable carriers and pharmaceutically acceptable carriers are similar, if not often identical, in nature.

Suitable pharmaceutically acceptable carriers include water, petroleum jelly (Vaseline™), petroleum, mineral oil, vegetable oil, animal oil, organic and inorganic waxes, such as microcrystalline, paraffin and ozocerite wax, natural polymers, such as xanthanes, gelatin, cellulose, collagen, starch, or gum arabic, alcohols, polyols, and the like. Also included are the carriers described hereinabove.

In another embodiment, the pharmaceutically acceptable carrier of the composition of the present invention includes a sustained release or delayed release carrier. The carrier can be any material capable of sustained or delayed release of the compound to provide a more efficient administration resulting in less frequent and/or decreased dosage of the compound, ease of handling, and extended or delayed effects on epithelial-related conditions. Non-limiting examples of such carriers include liposomes, microsponges, microspheres, or microcapsules of natural and synthetic polymers and the like. Liposomes which may enhance the localized delivery of the compounds of the inventive composition within skin layers, may be formed from a variety of phospholipids, such as cholesterol, stearylamines or phosphatidylcholines.

Suitable cosmetically acceptable carriers are described in the CTFA International Cosmetic Ingredient Dictionary and Handbook, 8th edition, edited by Wenninger and Canterbery, (The Cosmetic, Toiletry, and Fragrance Association, Inc., Washington, D.C., 2000), which is herein incorporated by reference. Also included are the carriers described hereinabove.

In another embodiment, the compositions of the present invention can further include one or more additional compatible active ingredients, which are aimed at providing the composition with another pharmaceutical, cosmeceutical or cosmetic effect, in addition to that provided by a compound of the inventive composition. "Compatible" as used herein means that the components of such a composition are capable of being combined with each other in a manner such that there is no interaction that would substantially reduce the efficacy of the composition under ordinary use conditions.

In one embodiment, the compound of the inventive compositions is an active ingredient.

As used herein, the phrase "additional active ingredient" refers to an agent, other than a compound of the inventive composition, that exerts a pharmacological, dermatological or any other beneficial activity. It is to be understood that "other beneficial activity" may be one that is only perceived as such by the subject using the inventive compositions.

In another embodiment, the compound of the inventive composition is a new excipient. As used herein a "new excipient" means any inactive ingredient that is intentionally added to the composition of the present invention and is not intended to exert therapeutic effects at the intended dosage, although it may act to improve product delivery. A new excipient is not fully qualified by existing safety data with respect to the currently proposed level of exposure, duration of exposure or route of administration. Additional characteristics of new excipients can be found in the Guidance for Industry Nonclinical Studies for the Safety Evaluation of Pharmaceutical Excipients issued by the US Food and Drug Administration Center for Drug Evaluation and Research, in May, 2005, herein incorporated by reference.

Compositions according to the present invention, which further include one or more additional active ingredients, can therefore be further efficiently used, in addition to their use as a treatment for an epithelial-related condition, in the treatment of any medical, cosmetic and/or cosmeceutical condition in which applying the additional active ingredient is beneficial.

Additional active ingredients included in the compositions according to the present invention used to treat an epithelial-related condition include, without limitation, one or more, in any combination, of a protective agent, an emollient, an astringent, an irritant, a keratolytic, a sun screening agent, a sun tanning agent, an antibiotic agent, an antifungal agent, an antiviral agent, an antiprotozoal agent, an anti-acne agent, an anesthetic agent, a steroidal anti-inflammatory agent, a non-steroidal anti-inflammatory agent, an antipruritic agent, an anti-oxidant agent, a chemotherapeutic agent, an anti-histamine agent, a vitamin, a hormone, an anti-dandruff agent, an anti-wrinkle agent, an anti-skin atrophy agent, a sclerosing agent, a cleansing agent, a caustic agent and a hypo-pigmenting agent.

In the broadest pharmacological sense, a "protective" is any agent that isolates the exposed surface of the skin or other membrane from harmful or annoying stimuli. Protectives as described herein may take the form of dusting powders, adsorbents, mechanical protective agents, and plasters. Dusting powders are relatively inert and insoluble materials that are used to cover and protect epithelial surfaces, ulcers and wounds. Usually, these substances are finely subdivided powders that absorb moisture and can act as a dessicant. The absorption of skin moisture decreases friction and also discourages certain bacterial growth. Some of the materials used as protective adsorbents include bentonite, insoluble salts of bismuth, boric acid, calcium carbonate, (precipitated), cellulose, corn starch, magnesium stearate, talc, titanium dioxide, zinc oxide, and zinc stearate.

Protectives also can be administered to the skin to form an adherent, continuous film that may be flexible or semi-rigid depending on the materials and the formulations as well as the manner in which they are applied. This material may serve several purposes including providing occlusion from the external environment, providing chemical support, and serving as vehicles for other medicaments. Mechanical protectives are generally either collodions or plasters. Examples include aluminum hydroxide gel, collodium, dimethicone, petrolatum gauze, absorbable gelatin film, absorbable gelatin sponge, zinc gelatin, kaolin, lanolin, anhydrous lanolin, mineral oil, mineral oil emulsion, mineral oil light, olive oil, peanut oil, petrolatum, silicones, hydrocolloids and the like.

In some embodiments, protectives included in the composition of the invention are demulcents. Demulcents are protective agents employed primarily to alleviate irritation, particularly mucous membranes or abraded tissues. They often are applied to the surface in a viscid, sticky preparation that covers the area readily and may be medicated. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

"Emollients" are generally bland, fatty or oleaginous materials which can be applied locally, particularly to the skin. Emollients increase the tissue moisture content, thereby rendering the skin softer and more pliable. Increased moisture content in the skin can be achieved by preventing water loss with an occlusive water-immiscible barrier, by increasing the water-holding capacity in the skin with humectants, or by altering the desquamation of the outermost skin layer, the stratum corneum. Useful emollients include lanolin, spermaceti, mineral oil, paraffin, petrolatum, white ointment, white petroleum, yellow ointment. Also included are vegetable oils, waxes, cetyl alcohol, glycerin, hydrophilic petrolatum, isopropyl myristate, myristyl alcohol, and oleyl alcohol.

"Astringents" are locally applied, generally protein precipitants, that have such a low cell penetrability that the action essentially is limited to the cell surface and interstitial spaces. The astringent action is accompanied by contraction and wrinkling of the tissue and by blanching. Astringents are used therapeutically to arrest hemorrhage by coagulating the blood, to promote healing, to toughen the skin or to decrease sweating. The principal components of astringents are salts of aluminum, zinc, manganese, iron or bismuth.

An "irritant" is a material that acts locally on the skin to induce, based on irritant concentration, hyperemia (meaning an excess of blood in an area or body part, usually indicated by red, flushed color or heat in the area), inflammation, and desiccation. Irritant agents include, but are not limited to, alcohol, aromatic ammonia spirits, benzoin tincture, camphor capsicum, and coal tar extracts. In some embodiments, the irritant is a rubefacient. As used herein "rubefacients" are agents that induce hyperemia, wherein hyperemia means an increased amount of blood in a body part or organ. Rubefaction, which is induced by rubefacients, results from increased circulation to an injured area and is accompanied by a feeling of comfort, warmth, itching and hyperesthesia.

"Keratolytics" (desquamating agents) act to remove outer layers of the stratum corneum. This is particularly useful in hyperkeratotic areas. The keratolytics include benzoyl peroxide, fluorouracil, resorcinol, salicylic acid, tretinoin, and the like.

Representative examples of sun screening agents usable in context of the present invention include, without limitation, p-aminobenzoic acid and its salts and derivatives thereof (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-propylene glycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzylacetone and benzylacetophenone; napthol-sulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene boman-2-one) and 4-isopropyl-di-benzoyl-methane, and any combination thereof.

Representative examples of sunless tanning agents usable in the present invention include, without limitation, dihydroxyacetone, glyceraldehyde, indoles and their derivatives. The sunless tanning agents can be used in combination with the sunscreen agents.

The term "antibiotic agent" as used herein means any of a group of chemical substances having the capacity to inhibit the growth of, or to destroy bacteria, and other microorganisms, used chiefly in the treatment of infectious diseases. Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefmetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones.

The term "anti-fungal agent" as used herein means any of a group of chemical substances having the capacity to inhibit the growth of or to destroy fungi. Anti-fungal agents include but are not limited to Amphotericin B, Candicidin, Dermostatin, Filipin, Fungichromin, Hachimycin, Hamycin, Lucensomycin, Mepartricin, Natamycin, Nystatin, Pecilocin, Perimycin, Azaserine, Griseofulvin, Oligomycins, Neomycin, Pyrrolnitrin, Siccanin, Tubercidin, Viridin, Butenafine, Naftifine, Terbinafine, Bifonazole, Butoconazole, Chlordantoin, Chlormidazole, Cloconazole, Clotrimazole, Econazole, Enilconazole, Fenticonazole, Flutrimazole, Isoconazole, Ketoconazole, Lanoconazole, Miconazole, Omoconazole, Oxiconazole, Sertaconazole, Sulconazole, Tioconazole, Tolciclate, Tolindate, Tolnaftate, Fluconawle, Itraconazole, Saperconazole, Terconazole, Acrisorcin, Amorolfine, Biphenamine, Bromosalicylchloranilide, Buclosamide, Calcium Propionate, Chlorphenesin, Ciclopirox, Cloxyquin, Coparaffinate, Diamthazole, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Triacetin, Ujothion, Undecylenic Acid, and Zinc Propionate.

The term "anti-viral agent" as used herein means any of a group of chemical substances having the capacity to inhibit the replication of or to destroy viruses used chiefly in the treatment of viral diseases. Anti-viral agents include, but are not limited to, Acyclovir, Cidofovir, Cytarabine, Dideoxyadenosine, Didanosine, Edoxudine, Famciclovir, Floxuridine, Ganciclovir, Idoxuridine, Inosine Pranobex, Lamivudine, MADU, Penciclovir, Sorivudine, Stavudine, Trifluridine, Valacyclovir, Vidarabine, Zalcitabine, Zidovudine, Acemannan, Acetylleucine, Amantadine, Amidinomycin, Delavirdine, Foscamet, Indinavir, Interferons (e.g., IFN-alpha), Kethoxal, Lysozyme, Methisazone, Moroxydine, Nevirapine, Podophyllotoxin, Ribavirin, Rimantadine, Ritonavir2, Saquinavir, Stailimycin, Statolon, Tromantadine, Zidovudine (AZT) and Xenazoic Acid.

The term "anti-protozoal agent" as used herein means any of a group of chemical substances having the capacity to inhibit the growth of or to destroy protozoans used chiefly in the treatment of protozoal diseases. Examples of antiprotozoal agents, without limitation include pyrimethamine (Daraprim®) sulfadiazine, and Leucovorin.

Examples of anti-acne agents include, without limitation, keratolytics, such as salicylic acid, sulfur, glycolic, pyruvic acid, resorcinol, and N-acetylcysteine; and retinoids such as retinoic acid and its derivatives (e.g., cis and trans, esters).

"Anesthetic agents" refers to agents that result in a reduction or loss of sensation. Non-limiting examples of anesthetic drugs that are suitable for use in the context of the present invention include pharmaceutically acceptable salts of lidocaine, bupivacaine, chlorprocaine, dibucaine, etidocaine, mepivacaine, tetracaine, dyclonine, hexylcaine, procaine, cocaine, ketamine, pramoxine and phenol.

"Steroidal anti-inflammatory agent", as used herein, refer to any one of numerous compounds containing a 17-carbon 4-ring system and includes the sterols, various hormones (as anabolic steroids), and glycosides. Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

"Non-steroidal anti-inflammatory agents" refers to a large group of agents that are aspirin-like in their action, including ibuprofen (Advil)®, naproxen sodium (Aleve)®, and acetaminophen (Tylenol)®. Additional examples of non-steroidal anti-inflammatory agents that are usable in the context of the present invention include, without limitation, oxicams, such as piroxicam, isoxicam, tenoxicam, sudoxicam, and CP-14,304; disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

"Antipruritic agents" as used herein refers to those substances that reduce, eliminate or prevent itching. Suitable antipruritic agents include, without limitation, pharmaceutically acceptable salts of methdilazine and trimeprazine.

"An anti-oxidant agent" as used herein refers to a substance that inhibits oxidation or reactions promoted by oxygen or peroxides. Non-limiting examples of anti-oxidants that are usable in the context of the present invention include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, glycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

"Chemotherapeutic agent" refers to chemicals useful in the treatment or control of a disease. Non-limiting examples of chemotherapeutic agents usable in context of the present invention include daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A and XR9576.

"Antihistamine agent" as used herein refers to any of various compounds that counteract histamine in the body and that are used for treating allergic reactions (such as hay fever) and cold symptoms. Non-limiting examples of antihistamines usable in context of the present invention include chlorpheniramine, brompheniramine, dexchlorpheniramine, tripolidine, clemastine, diphenhydramine, promethazine, piperazines, piperidines, astemizole, loratadine and terfenadine.

"Vitamin" as used herein, refers to any of various organic substances essential in minute quantities to the nutrition of most animals; vitamins act especially as coenzymes and precursors of coenzymes in the regulation of metabolic processes. Non-limiting examples of vitamins usable in context of the present invention include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

"Hormone" as used herein refers to natural substances produced by organs of the body that travel by blood to trigger activity in other locations or their synthetic analogs. Suitable hormones for use in the context of the present invention include, but are not limited to, calciferol (Vitamin D3) and its products, androgens, estrogens and progesterones.

"Anti-dandruff agents" as used herein refer to agents that reduce, eliminate or prevent a scurf from forming on skin, especially of the scalp, that comes off in small white or grayish scales. Exemplary anti-dandruff ingredients usable in context of the present invention include, without limitation, zinc pyrithione, shale oil and derivatives thereof such as sulfonated shale oil, selenium sulfide, sulfur; salicylic acid, coal tar, povidone-iodine, imidazoles such as ketoconazole, dichlorophenyl imidazolodioxalan, clotrimazole, itraconazole, miconazole, climbazole, tioconazole, sulconazole, butoconazole, fluconazole, miconazolenitrite and any possible stereo isomers and derivatives thereof such as anthralin, piroctone olamine (Octopirox), selenium sulfide, and ciclopiroxolamine, and mixtures thereof.

"Anti-skin atrophy actives" refers to substances effective in replenishing or rejuvenating the epidermal layer by promoting or maintaining the natural process of desquamation. Examples of antiwrinkle and antiskin atrophy actives which can be used in context of the present invention include retinoic acid, its prodrugs and its derivatives (e.g., cis and trans) and analogues; salicylic acid and derivatives thereof, sulfur-containing D and L amino acids and their derivatives and salts, particularly the N-acetyl derivatives, a preferred example of which is N-acetyl L-cysteine; thiols, e.g. ethane thiol; alpha-hydroxy acids, e.g. glycolic acid, and lactic acid; phytic acid, lipoic acid; lysophosphatidic acid, and skin peel agents (e.g., phenol and the like). Sclerosing agents or sclerosants may be also employed. A "sclerosant" refers to an agent used as a chemical irritant injected into a vein in sclerotherapy. The most common ones are morrhuate sodium, sodium tetradecyl sulfate, laureth 9 and ethanolamine oleate.

Cleansing agents which may be used in the present invention include surfactant based cleansing agents, examples of which have been listed hereinabove. Other non-surfactant-based cleansing agents known to those of skill in the art may also be employed.

"Caustic agents" refer to substances capable of destroying or eating away epithelial tissue by chemical action. Caustic agents can be used to remove dead skin cells. For example, beta-hydroxy acids, naturally derived acids with a strong kerolytic effect, are useful for problem skin, acne or peeling.

"Hypopigmenting agents" refer to substances capable of depigmenting the skin. Suitable hypopigmenting agents include hydroquinones, mequinol, and various protease inhibitors including serine protease inhibitors, active soy and retinoic acid.

The topical compositions of the present invention can be applied locally to the skin and may be in any form including solutions, oils, creams, ointments, gels, lotions, shampoos, milks, cleansers, moisturizers, sprays, skin patches and the like.

In another embodiment, a compound of the present invention, a carrier and, optionally, additional active ingredients are formed into a composition comprising a solution, emulsion or gel suspension.

In some embodiments, a compound of the present invention, a pharmaceutical or cosmetic carrier and, optionally, one or more additional active ingredients are in the form of a solution. A solution can be prepared by mixing a solute or dissolved substance (such as a compound of the invention and, optionally, one or more active ingredient(s)) uniformly throughout a solvent carrier such as water or organic solvents, such as the alcohols (e.g. ethanol or isopropanol, acetone).

In another preferred embodiment, a composition comprising a compound of the present invention, a carrier and other, optional ingredients can be dispersed in an emulsion. An emulsion is a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will not occur unless a third substance, an emulsifying agent, is incorporated. Thus, a basic emulsion contains at least three components, the two immiscible liquid carriers and the emulsifying agent as well as the compound of the invention. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil.

Emulsifying agent carriers useful in the present invention are described hereinabove.

When the composition of the invention is an emulsion including a compound of the invention, non-lipid-based vehicles are particularly useful due to the lipophilic nature of the compounds.

In another embodiment, a composition containing a compound of the present invention can be mixed with a gel suspension, (a semi-solid carrier) or solid carrier to form a paste, powder, ointment, cream, lotion, hydrogel or the like.

For example, ointments may be prepared which are in gel-suspension form. These are semi-solid preparations intended for external application to the epithelium. Generally, ointment bases are categorized into hydrocarbon bases (oleaginous), which may use white petroleum as a base; adsorption bases (anhydrous), which may use hydrophilic petroleum or anhydrous lanolin; emulsion bases (water and oil type); emulsion bases (oil and water type); and water soluble bases, which often use polyethylene glycol as an ointment base.

Additional compositions of the present invention can be readily prepared using technology which is known in the art such as described in Remington's Pharmaceutical Sciences, 18th or 19th editions, published by the Mack Publishing Company of Easton, Pa. incorporated herein by reference in it entirety.

In some embodiments, the compositions of the present invention include about 0.001% to about 10.0% w/w of a compound of the present invention.

According to another aspect of the present invention, there is provided a method of preparing the compositions described hereinabove. The process generally includes admixing the at least one compound of the present invention, as described hereinabove, and the pharmaceutically, cosmetically or cosmeceutically acceptable carrier. In cases where additional active ingredients, as detailed above, are present in the compositions, the process includes admixing these ingredients together with the active ingredients and the carrier. The mixing technique utilized in the process of the present invention can involve any one of the known techniques for formulating topical compositions. A variety of exemplary formulation techniques that are usable in the process of the present invention is described, for example, in Harry's Cosmeticology, Seventh Edition, Edited by J B Wilkinson and R J Moore, Longmann Scientific & Technical, 1982 incorporated herein by reference in its entirety.

According to another aspect of the present invention, there is provided a method of treating a medical, cosmetic and/or cosmeceutical condition associated with epithelial tissues that comprises hair loss. The method is effected by topically applying, a pharmaceutically, cosmetically or cosmeceutically effective amount of the composition of the present invention as described above onto a surface.

As used herein the terms "pharmaceutically effective amount", "cosmetically effective amount", or "cosmeceutically effective amount" refer to the amount of any of the compositions of the invention that result in a therapeutic or beneficial effect following its administration to a subject. The pharmaceutical, cosmeceutical, or cosmetic effect can be curing, minimizing, preventing or ameliorating a disease or disorder, improving the physical appearance and aesthetics, or may have any other pharmaceutical, cosmeceutical or cosmetic beneficial effect. The concentration of the substance is selected so as to exert its pharmaceutical, cosmeceutical or cosmetic effect, but low enough to avoid significant side effects within the scope and sound judgment of the skilled artisan. The effective amount of the composition may vary with the particular epithelial tissue being treated, the age and physical condition of the biological subject being treated, the severity of the condition, the duration of the treatment, the nature of concurrent therapy, the specific compound, composition or other active ingredient employed, the particular carrier utilized, and like factors.

A skilled artisan can determine a pharmaceutically effective amount of the inventive compositions by determining the unit dose. As used herein, a "unit dose" refers to the amount of inventive composition required to produce a response of 50% of maximal effect (i.e. $ED_{50}$). The unit dose can be assessed by extrapolating from dose-response curves derived from in vitro or animal model test systems.

According to some embodiments of the present invention, the compositions of the present invention are applied topically as needed. According to some embodiments, the inventive compositions are topically applied between one and four times a day. According to some embodiments, the inventive compositions are applied topically twice a day (e.g., once in the morning and once in the evening). According to some embodiments, the topical application of the compositions of the present invention is carried out daily. Some conditions may require topical application for an indeterminate length of time.

In one embodiment, the inventive compositions are topically administered to the epithelial surface of a subject. Non limiting examples of epithelial surfaces onto which the compositions of the present invention can be applied topically include the lateral aspect of forearms, the lateral aspect of legs, elbows, feet, backhands, back, scalp, face, eyebrows, eyelids, lip, and any other skin surfaces, and any mucosal membrane described herein.

Alternatively, the compositions may be administered to the epithelial condition as a component of, for example, a bandage, adhesive, or transdermal patch. In these instances, the compositions may be an integral component of the bandage, adhesive, or transdermal patch and are thereby applied to the epithelial surface.

As used herein the term "treating" includes abrogating, substantially inhibiting, slowing or reversing the progression of a condition, substantially ameliorating clinical or aesthetical symptoms of a condition, substantially preventing the appearance of clinical or aesthetical symptoms of a condition, protecting from harmful or annoying stimuli or generally promoting healthy epithelial tissue.

The term "condition" includes a variety of conditions related to skin or mucosal membranes. This term is meant to include disorders or diseases, the promotion of healthy epithelium; dry skin; and inflammation caused by any underlying mechanism or disorder.

In some embodiments, the compositions of the invention are administered to treat a skin condition that is already present, such as, but not limited to, alopecia.

The topical therapeutic compositions may be formulated as ophthalmic preparations to treat alopecia of the eyelashes and alopecia of the eyebrows. Ophthalmic preparations for topical administration can include (pharmaceutical) carriers such as sterile and non-sterile aqueous solutions, non-aqueous solutions in common solvents such as alcohols, or solutions comprising a compound of Formula I in liquid or solid oil bases. Such preparations can be prepared readily using technology known in the art, for example, as described in "The Art, Science and Technology of Pharmaceutical Compounding," Second Edition, edited by Loyd V. Allen, Jr., Ph.D., and published by the American Pharmaceutical Association of Washington D.C., and in "Remington's Pharmaceutical Sciences," 18th or 19th Editions, published by the Mack Publishing Company of Easton, Pa. incorporated herein by reference in its entirety. In preparing an ophthalmic product, a skilled artisan will take into consideration a number of general considerations, including sterility, buffer capacity and pH, tonicity, viscosity, stability, additives, particle size, packaging and preservatives.

Sterile isotonic solutions, properly preserved, are suitable for preparing ophthalmic solutions. In most cases, when the concentration of the active ingredient is low, i.e., less than about 2.5% to about 3.0%, the active ingredient can be dissolved directly in the isotonic vehicle. In some embodiments, compatible excipients, such as preservatives, antioxidants and viscosity enhancers, may be added. For comfort during administration, ophthalmic and nasal solution dosage forms must be "isotonic" with body fluids.

Ophthalmic suspensions are dispersions of finely divided, relatively insoluble ingredients in an aqueous vehicle containing suitable suspending and dispersing agents. Dosage uniformity often requires brisk shaking of the suspension to distribute the suspended substance. The size of particles in an ophthalmic suspension must be micronized so that the particles are small enough to not irritate the eye.

Ophthalmic ointments offer the advantage of longer contact time and greater total bioavailability. The amount of solid released in unit time is a function of concentration, solubility in the ointment base, and diffusivity of the substance in the base. Ophthalmic ointments are prepared so that they do not irritate the eye, do permit diffusion of the active ingredient, and do retain the activity of the active ingredient for a reasonable period of time when stored properly. White petrolatum is the base primarily used for ophthalmic ointments. Powders incorporated in the preparation must be micronized and sterilized to ensure that the final product is nongritty and thus nonirritating.

The present invention described hereinabove has both human and veterinary utility. The term "subject" as used herein includes animals of mammalian origin. The present invention has utility in human subjects.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Compositions of the present invention can be prepared readily using technology which is known in the art such as described in Remington's Pharmaceutical Sciences, 18th or 19th editions, published by the Mack Publishing Company of Easton, Pa., which is incorporated herein by reference.

Example 1

Bovine Cornea Hydrolysis Assay

The cellular effects of $PGF_{2\alpha}$ in vivo are mediated by a G protein-coupled transmembrane receptor designated the FP receptor (O. Saito et al, Am J. Physiol. Renal Physiol. 284(6): F1164-70 (2003)). Woodward et. al used an isolated feline iris sphincter, where prostanoid FP receptors and prostamide receptors coexist, as a test system to show that prostaglandin-ethanolamides (prostamides) produce their effects by interacting with receptive targets distinct from prostaglandin receptors (David F. Woodward, et al., "Identification of an Antagonist That Selectively Blocks the Activity of Prostamides (Prostaglandin-Ethanolamides) in the Feline Iris," Br. J. Pharmacol. 150(3):352-52 (2007)).

A *bovine* cornea hydrolysis test system (K. M. Maxey, et al., "The Hydrolysis of Bimatoprost in Corneal Tissue Generates a Potential Prostanoid FP Receptor Agonist," Survey of Ophthalmology, 47 (Suppl 1):S34-40 (2002)) has been used to determine whether four test compounds of the present invention, namely 16-phenoxy $PGF_{2\alpha}$ cyclopropyl amide; 17-phenyl trinor $PGF_{2\alpha}$ cyclopropyl amide; 16-phenoxy $PGF_{2\alpha}$ cyclopropyl methyl amide; and 17-phenyl trinor $PGF_{2\alpha}$ cyclopropyl methyl amide, react similarly to bimatoprost in this test system.

Method

Bovine corneas are excised within 1-2 hour of death. For each compound tested, one cornea (0.6 g) is placed into an 18 mm×150 mm glass test tube containing 10 ml of phosphate-buffered saline ("PBS") at pH 7.4. The compound of interest (250 μg in about 120 μl ethanol) is added to each test tube containing a cornea and to a tube containing only 10 ml of PBS (no cornea), which served as a negative control. Test tubes are covered with parafilm and incubated at 37° C. with shaking.

After the first time point, a 5 ml aliquot is removed from each test tube and transferred into another marked test tube. The remaining material continues to incubate at 37° C. until subsequent test time point(s) is/are reached. For each test tube, 1.0 ml of 5% $KHSO_4$ is added to bring the pH down to about 3 and sufficient NaCl is added to saturate the solution; the solution then is extracted three times with 80% ethyl acetate-hexane. The solvent is evaporated under nitrogen, dissolved in 200 μl of 80% ethyl acetate-hexane, and the 200 μl sample then transferred to a 2 ml screw cap vial. Samples are stored at −20° C. until run on an HPLC column.

After the second time point, the cornea is removed from each experimental test tube. For each test tube, 1.0 ml of 5% $KHSO_4$ is added to bring the pH down to about 3 and sufficient NaCl added to saturate the solution; the solution then is extracted three times with 80% ethyl acetate-hexane. The solvent is evaporated under nitrogen, dissolved in 200 μl of 80% ethyl acetate-hexane, and the 200 μl sample then transferred to 2 ml screw cap vials. Samples are stored at −20° C. until they are run on an HPLC column.

For HPLC, samples are run on a Beckman Ultrasphere ODS analytical C18 HPLC column (5μ, 4.6 mm×25 cm) at 1 ml/min using either 60:40:0.1 or 70:30:0.1 methanol:water:acetic acid as solvent. Absorbance is monitored at 210 nm.

Results

Hydrolysis data for four test compounds of the present invention, namely 16-phenoxy $PGF_{2\alpha}$ cyclopropyl amide; 17-phenyl trinor $PGF_{2\alpha}$ cyclopropyl amide; 16-phenoxy $PGF_{2\alpha}$ cyclopropyl methyl amide; and 17-phenyl trinor $PGF_{2\alpha}$ cyclopropyl methyl amide, are shown in Table 1.

TABLE 1

| Compound | % Hydrolyzed after 12 hr |
|---|---|
| bovine cornea hydrolysis | |
| 17-phenyl trinor $PGF_{2\alpha}$ cyclopropyl methyl amide (negative control) | 0 |
| 17-phenyl trinor $PGF_{2\alpha}$ cyclopropyl methyl amide (cornea sample 1) | 1.1 |
| 17-phenyl trinor $PGF_{2\alpha}$ cyclopropyl methyl amide (cornea sample 2) | 0.83 |
| 17-phenyl trinor $PGF_{2\alpha}$ cyclopropyl methyl amide (cornea sample 3) | 0.8 |
| Avg | 0.91% |
| 16-phenoxy $PGF_{2\alpha}$ cyclopropyl amide (negative control) | 0 |
| 16-phenoxy $PGF_{2\alpha}$ cyclopropyl amide (cornea sample 1) | 2.0 |
| 16-phenoxy $PGF_{2\alpha}$ cyclopropyl amide (cornea sample 2) | 1.89 |
| 16-phenoxy $PGF_{2\alpha}$ cyclopropyl amide (cornea sample 3) | 1.44 |
| Avg | 1.78% |
| 17-phenyl trinor $PGF_{2\alpha}$ cyclopropyl amide (negative control) | 0 |
| 17-phenyl trinor $PGF_{2\alpha}$ cyclopropyl amide (cornea sample 1) | 1.31 |
| 17-phenyl trinor $PGF_{2\alpha}$ cyclopropyl amide (cornea sample 2) | 2.0 |
| 17-phenyl trinor $PGF_{2\alpha}$ cyclopropyl amide (corneal sample 3) | 2.15 |
| Avg | 1.82% |
| 16-phenoxy $PGF_{2\alpha}$ cyclopropyl methyl amide (negative control) | 0 |
| 16-phenoxy $PGF_{2\alpha}$ cyclopropyl methyl amide (cornea sample 1) | 1.28 |
| 16-phenoxy $PGF_{2\alpha}$ cyclopropyl methyl amide (cornea sample 2) | 1.18 |
| 16-phenoxy $PGF_{2\alpha}$ cyclopropyl methyl amide (cornea sample 3) | 1.2 |
| Avg | 1.22% |

Conclusion

It appears that the HPLC profiles resulting from the hydrolysis experiments for these four test compounds are different from the profile published for bimatoprost.

Example 2

Use for Restoring Eyelashes

In one embodiment, the composition of the present invention is a transparent gel formulated according to Table 2. The formulation comprises water, at least one prostaglandin analog according to the present invention (concentration about 0.001% to about 0.05% w/w of the composition); a thickener, optionally a hair stimulating agent; caffeine, and at least one penetrating agent and the pH adjusted to 7.2. The gel is applied as a fine line at the skin-eyelash border every night on clean dry eyes. The gel is aqueous enough to spread to the hair follicles but thick enough not to drip.

TABLE 2

Transparent Gel Formulation I

| Ingredient | Range (expressed as percent by weight) |
| --- | --- |
| Water | 50-99.95 |
| Pentylene glycol | 2.00-20.00 |
| Ethanol | 0.1-15.00 |
| Propylene glycol alginate | 0.23-3.00 |
| Acrylates/C10-30 Alkyl acrylate crosspolymer | 0.10-1.00 |
| Butyl glycol | 0.50-10.00 |
| Caffeine | 0.05-4.00 |
| Oleanolic Acid | 0.001-0.1 |
| PPG-26-Buteth-26 | 0.001-1.0 |
| Propylene glycol | 0.1-10 |
| Apigenin | 0.001-0.1 |
| Biotinoyl tripeptide-1 | 0.00001-0.1 |
| Tetrahydroxypropyl Ethylene diamine | 0.1-2.00 |
| Cyclopropyl 7-(3,5-dihydroxy-2-(3-hydroxy-4-phenoxy-but-1-enyl)-cyclopentyl)-hept-5-enamide | 0.001-5.00 |
| Tetrasodium EDTA | 0.01-0.25 |
| Disodium phosphate | 0.001-1.00 |
| Sodium Phosphate | 0.001-1.00 |
| Diazolidinyl Urea | 0.05-0.30 |
| Methylparaben | 0.05-0.70 |
| Propylparaben | 0.01-0.70 |

In another embodiment, the composition is a transparent gel formulated to comprise at least one of 16-phenoxy $PGF_{2\alpha}$ cyclopropyl amide; 17-phenyl trinor $PGF_{2\alpha}$ cyclopropyl amide; 16-phenoxy $PGF_{2\alpha}$ cyclopropyl methyl amide; or 17-phenyl trinor $PGF_{2\alpha}$ cyclopropyl methyl amide (concentration about 0.001% to about 0.05% w/w of the composition) plus the following ingredients (Table 3):

TABLE 3

| Ingredient | Percent (by weight) |
| --- | --- |
| Water | 91.0368% |
| Pentylene glycol | 3% |
| Ethanol | 0.95% |
| Propylene glycol alginate | 0.5% |
| Acrylates/C10-30 Alkyl acrylate crosspolymer | 0.3% |
| Butyl glycol | 2.0% |
| Caffeine | 0.5% |
| Oleanolic Acid | 0.001% |
| PPG-26-Buteth-26 | 0.01% |
| Propylene glycol | 0.56% |
| Apigenin | 0.001% |
| Biotinoyl tripeptide-1 | 0.0005% |
| Tetrahydroxypropyl Ethylene diamine | 0.5% |
| Cyclopropyl 7-(3,5-dihydroxy-2-(3-hydroxy-4-phenoxy-but-1-enyl)-cyclopentyl)-hept-5-enamide | 0.05% |
| Tetrasodium EDTA | 0.05% |
| Disodium phosphate | 0.097% |
| Sodium Phosphate | 0.0037% |
| Diazolidinyl Urea | 0.3% |
| Methylparaben | 0.11% |
| Propylparaben | 0.03% |

Test formulations contained either 0.025% or 0.05% 16-phenoxy PGF2α cyclopropyl amide. The formulation containing 0.025% 16-phenoxy PGF2α cyclopropyl amide was used on the left side, and the formulation containing 0.05% 16-phenoxy PGF2α cyclopropyl amide was used on the right side. Test formulations were given randomly to volunteers without consideration of coloration of eyelashes, race, ethnicity or sex. Unless otherwise noted there was no significant difference observed for the left versus the right side.

Subject K. M. was a female age 50 whose original eyelash color was light. Some thickening was seen within 10 days. Increase in length was obvious by about 3 weeks. The increase in length was estimated as about 55%. The lashes were darker, fuller and showed an upward curving angle of growth.

Subject B. J. H was a female age 42 whose original eyelash color was light. Eyelashes exhibited obvious growth by week 3. Lashes were much thicker, fuller, longer and curvier than before use. Increase in length was approximately 80% and the thickness of the lashes approximately doubled.

Subject K. Y. was a female age 37 whose original eyelash color was dark. Lashes grew so much that by week 4 the test was discontinued because eyelashes were too long. Noticeable results at week 1.

Subject S. V. was a female age 31. By week one, thickness increased noticeably. By week 4, observed about 50% increase in length of lashes. Lashes appeared darker, fuller, and longer. Lashes improved somewhat after that but peak result, with some lashes 100% longer, was at 6 weeks.

Subject T. D. was a female age 51, whose original eyelash color was dark but who had poor eyelash length, curve and thickness. Subject noticed an improvement as early as 1 week. By 3 weeks, lashes were 40% longer, thicker and darker and curled upwards. Product continued to improve eyelash condition. After two months, increase in length was approximately 55%. Right side was faster to grow.

Subject J. P. was a female, age 59. Eyelashes were visibly darker and thicker within 1 week. Increase in length was noticeable by 2 weeks. Improvement peaked at about 6 weeks with approximately a 45% increase in length and 60% increase in numbers of eyelashes.

Subject M. M. was a female, age 59. The subject saw general improvement in as little as 1 week. Definite and noticeable improvement by 2 weeks. Estimated increase in length by 4 weeks was 50% Subject thought right side was better.

Subject R. W. was a female, age 59 with dark eyelashes. Eyelashes were much thicker after 2 weeks. Approximately 60% increase in max length at 5 weeks.

Subject J. T. was a female, age 38 with light eyelashes. Eyelashes became much darker, thicker and approximately 60% longer within 4 weeks. Noticed general improvement in about 2 weeks.

Subject L. H. was a female, age 55 with light eyelashes. Improvement in eyelash quality was noticeable by week 3. By week 5 eyelashes were about 100% longer than baseline, darker, and curved upwards.

Subject A. E. was a female, age 42 having a dry eye condition. The subject tolerated the product well. Visible results apparent starting as early as 1 week. At the end of the test (6 weeks), eyelashes were longer (increase 50%), darker, and thicker.

Subject F. P, a female age 48 had worn false eyelashes for long periods. Her lashes were badly damaged and were very short and broken. Subject had had Lasik surgery and had dry eye. Subject tolerated the product. No noticeable improvement was seen for 2-3 weeks. Suddenly the lashes started to get longer, thicker and darker. Final improvement was approximately 45% of original length and approximately 60% thicker.

Subject J. M., a male, age 51 had short, dark eyelashes. After 2 weeks, improvement was noticeable. By 4 weeks, lashes were bushy, very thick, dark, and length was increased 50%.

Subject D. T., a female age 31, had very sparse, thin, dark, short eyelashes. Improvement was noticed by 2 weeks. Final result at 5 weeks was increase in length by approximately 45% in length, 30% increase in numbers, and lashes curled up. Subject thought left side was better.

Subject D. C., an Asian female, age 31, had eyelashes that did not protrude below the eyelid. After 3-4 weeks, eyelashes had grown to the point of clear visibility below lids. Estimate of increase in length 50%, thickness 100%, and lashes curled up.

Subject B. R., a male, age 60, had light eyelashes. Product was applied to one side only. There was a clear difference in sides by 2 weeks. Final increase in length 45%, darker, thicker and lashes curled up.

Subject V. M., a female age 55. Lashes showed noticeable improvement by 2 weeks in terms of length, thickness and curve. Also applied to eyebrows which were sparse particularly at ends. Final result was approximately 60% increase in length and 50% increase in numbers.

Subject G. F., a female, age 55, had short, thin eyelashes. Positive improvement seen starting at 2 weeks. Lashes doubled in length (100%) increase, almost 100% thicker, darker, and curled upwards.

Subject S. M., a female age 45, noticed improvement noted by 1 week. At week 3, lashes were 30% longer, thicker and curled. By 6 weeks, length had improved by 50%.

Subject J. Z a female, age 60, showed noticeable improvement by 2 weeks. Final result was increase in length by 45-50%. Lashes were darker and more upturned.

Subject A. T., a female, age 50, showed improvement after 2 weeks. Noticeable improvement after 4 weeks even without mascara. Subject thought left side was better.

Example 3

Use for Restoring Eyebrows

A composition prepared according to the present invention is formulated as a transparent gel as described in the two described embodiments of Example 2. The formulation comprises water, at least one prostaglandin analog according to the present invention (concentration about 0.001% to about 0.05% w/w of the composition); a thickener, optionally a hair stimulating agent; caffeine, and at least one penetrating agent and the pH adjusted to 7.2. The gel is applied by brush as a line at the browbone every night on clean, oil-free brows in the absence of makeup. The gel is sufficiently aqueous to spread to the hair follicles but thick enough not to drip.

Test formulations contained either 0.025% or 0.05% 16-phenoxy PGF2α cyclopropyl amide. The formulation containing 0.025% 16-phenoxy PGF2α cyclopropyl amide was used on the left side, and the formulation containing 0.05% 16-phenoxy PGF2α cyclopropyl amide was used on the right side. Test formulations were given randomly to volunteers without consideration of coloration of eyelashes, race, ethnicity or sex. Unless otherwise noted there was no significant difference observed for the left versus the right side.

Subject K. P.: brows showed a noticeable increase in number of hairs and color after 2 weeks.

Subject G. F., a female, age 55. Product was applied to a bald spot in brow that had been absent for 40 years. Hairs started to fill in.

Example 4

Use for Restoring Scalp Hair

A composition prepared according to the present invention may be formulated as an aerosol spray, a topical cream, ointment or a solution.

An aerosol containing approximately 0.005% to about 5.0% (w/w) of at least one prostaglandin analog according to the present invention is prepared by dissolving the analog in absolute alcohol. The resulting solution is filtered and chilled to about −30° C. A chilled mixture of dichlorodifluoromethane and dichlorotetrafluoroethane is added to the solution. Plastic-coated amber bottles are cold filled with the resulting solution and capped. About 1 cc of the formulation is sprayed on the scalp daily at night.

A topical cream is prepared as follows. Tegacid and spermaceti are melted together at a temperature of about 70° C. to about 80° C. Methylparaben is dissolved in water and propylene glycol, polysorbate 80, and at least one prostaglandin analog (about 0.005% to about 5.0% (w/w)) are added in turn, maintaining the temperature at about 75-80° C. The methylparaben mixture is added slowly to the tegacid and spermaceti melt with constant stirring for at least 30 minutes, with additional stirring until the temperature has dropped to 40-45° C. Finally, sufficient water is added to bring the final weight to 10000 gm and the preparation is stirred to maintain homogeneity until cooled and congealed. The formulation is applied nightly.

A topical ointment containing at least one prostaglandin analog (about 0.001% to about 5.0% (w/w)) is prepared as follows: White petrolatum and wool fat are melted, strained, and liquid petrolatum added. At least one prostaglandin analog of the present invention is added; optionally zinc oxide and calamine may be added as well. The mixture is milled until the powders are finely divided and uniformly dispersed. The mixture is stirred into the white petrolatum, melted and cooled with stirring until the ointment congeals. The formulation is applied nightly.

Subject B. R., male, age 60: transparent gel formulation from Example 1 and Example 2 was applied to scalp at 1% concentration. Improvement in bald area, with dark hairs filling in from sides and darkening of certain gray areas, was seen.

Example 5

Use for Restoring Hair Color

A composition prepared according to the present invention is formulated as an aerosol spray, a topical cream, ointment or a solution. The total volume used is about 1 cc per application. The formulation is applied nightly. The concentration of the prostaglandin analog in the composition is about 0.001% to about 5.0% (w/w).

Subject B. R., male, age 60: transparent gel formulation from Example 1 and Example 2 was applied to scalp at 1% concentration. Improvement in bald area, with dark hairs filling in from sides and darkening of certain gray areas, was seen.

While the present invention has been described with reference to the specific embodiments thereof, it should be understood by those skilled in the art that various changes may be made and equivalents may be substituted without departing from the true spirit and scope of the Invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A topical composition for treating an epithelial-related condition, wherein the epithelial-related condition is a condition selected from the group consisting of sparse hair growth, short hair growth, thin hair growth, alopecia, and hair depigmentation, comprising:

(a) a compound of formula XI or a salt of formula XI:

[Formula XI]

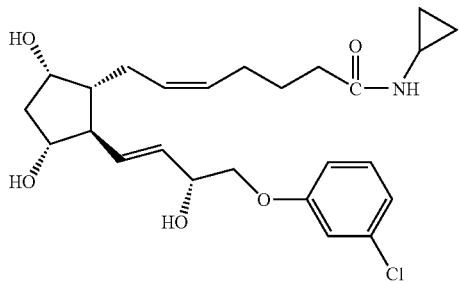

wherein
the simple straight line represents a bond lying approximately in the surface plane; the wedge shaped bond is directed to the front of surface plane; and the hatched bond is directed in the back of the surface plane;
wherein the compound of formula XI is 16-(3-chlorophenoxy)-17, 18, 19, 20-tetranor PGF$_{2\alpha}$ cyclopropyl amide; whereby the composition stimulate hair growth on an epithelial surface to which the composition has been applied;
and
(b) a carrier.

2. The topical composition according to claim 1, wherein the composition is an ophthalmic composition.

3. The topical composition according to claim 1, wherein the composition restores pigmentation to depigmented hair.

4. The topical composition according to claim 1, wherein the epithelial-related condition is alopecia.

5. The topical composition according to claim 1, wherein the epithelial surface onto which the composition is applied topically is an eyelid.

6. The topical composition according to claim 1, wherein the epithelial-related condition is alopecia of at least one eyelash.

7. The topical composition according to claim 1, wherein the epithelial surface onto which the composition is applied topically is a face.

8. The topical composition according to claim 1, wherein the condition is alopecia of at least one eyebrow.

9. The topical composition according to claim 1, wherein the epithelial surface onto which the composition is applied topically is a scalp.

10. The composition according to claim 1, wherein the epithelial surface onto which the composition is applied topically is above a lip.

11. The topical composition of claim 1, wherein the compound of (a) is present in a pharmaceutically effective amount.

12. The topical composition of claim 1, wherein the compound of (a) is present in a cosmetically effective amount.

13. The topical composition of claim 1, wherein the compound of (a) is present in a cosmeceutically effective amount.

* * * * *